(12) United States Patent
Jung et al.

(10) Patent No.: US 9,564,603 B2
(45) Date of Patent: Feb. 7, 2017

(54) HETEROCYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Hye-Jin Jung, Yongin (KR); Seok-Hwan Hwang, Yongin (KR); Young-Kook Kim, Yongin (KR); Jun-Ha Park, Yongin (KR); Eun-Young Lee, Yongin (KR); Jong-Woo Kim, Yongin (KR); Jin-O Lim, Yongin (KR); Sang-Hyun Han, Yongin (KR); Kwang-Hyun Kim, Yongin (KR); Eun-Jae Jeong, Yongin (KR); Soo-Yon Kim, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 299 days.

(21) Appl. No.: 14/284,964

(22) Filed: May 22, 2014

(65) Prior Publication Data

US 2015/0053941 A1 Feb. 26, 2015

(30) Foreign Application Priority Data

Aug. 22, 2013 (KR) .................. 10-2013-0099919

(51) Int. Cl.
*H01L 51/00* (2006.01)
*C07D 401/14* (2006.01)
(Continued)

(52) U.S. Cl.
CPC ......... *H01L 51/0072* (2013.01); *C07D 209/56* (2013.01); *C07D 401/14* (2013.01);
(Continued)

(58) Field of Classification Search
None
See application file for complete search history.

(56) References Cited

U.S. PATENT DOCUMENTS 7,429,372 B2    9/2008  Pez et al.
2007/0231503 A1* 10/2007  Hwang ................ C09K 11/06
                                                    428/1.1
(Continued)

FOREIGN PATENT DOCUMENTS

KR    10-2014-0050388 A    4/2014
KR    10-2014-0050389 A    4/2014

OTHER PUBLICATIONS

M.A. Baldo, et al., "Highly efficient phosphorescent emission from organic electroluminescent devices", Letters to Nature, Nature, vol. 395, Sep. 10, 1998, pp. 151-154.
(Continued)

*Primary Examiner* — J. L. Yang
(74) *Attorney, Agent, or Firm* — Lee & Morse, P.C.

(57) ABSTRACT

A heterocyclic compound and an organic light-emitting diode including the same, the heterocyclic compound being represented by Formula 1, below:

(Continued)

<Formula 1>

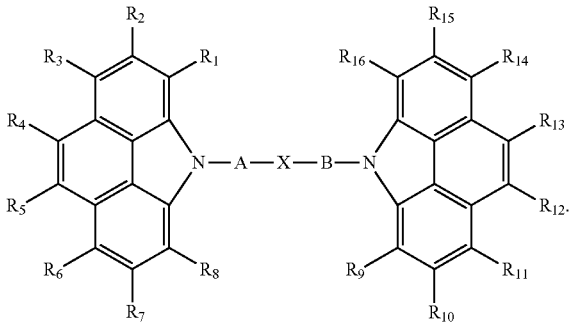

20 Claims, 1 Drawing Sheet

(51) Int. Cl.
 C07D 209/56 (2006.01)
 H01L 51/50 (2006.01)
(52) U.S. Cl.
 CPC ...... H01L 51/0052 (2013.01); H01L 51/0058 (2013.01); H01L 51/0067 (2013.01); *H01L 51/0081* (2013.01); *H01L 51/0085* (2013.01); *H01L 51/5016* (2013.01)

(56) References Cited

U.S. PATENT DOCUMENTS

2009/0019768 A1    1/2009  Toseland et al.
2014/0110675 A1    4/2014  Kim et al.
2014/0110676 A1    4/2014  Kim et al.
2015/0171353 A1*   6/2015  Jeong .................. H01L 51/0094
                                                      257/40

OTHER PUBLICATIONS

M.A. Baldo, et al., "Very high-efficiency green organic light-emitting devices based on electrophosphorescence", Applied Physics Letters, vol. 75, No. 1, Jul. 5, 1999, pp. 4-6.
Raymond C. Kwong, et al., "High operational stability of electrophosphorescent devices" Applied Physics Letters, vol. 81, No. 1, Jul. 1, 2002, pp. 162-164.
Chihaya Adachi, et al., High-efficiency organic electrophosphorescent devices with tris(2-phenylpyridine) iridium dopes into electron-transporting materials, Applied Physics Letters, vol. 77, No. 6, Aug. 7, 2000, pp. 904-906.
2009 Fall Assembly and Symposium vol. 34, No. 2, 2009.

* cited by examiner

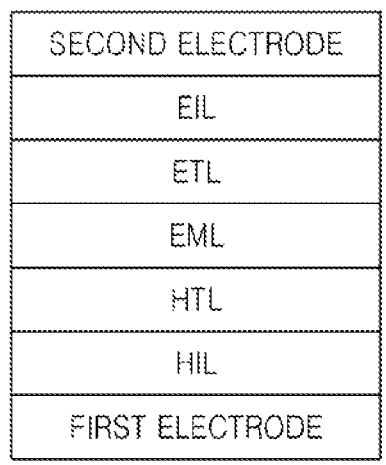

HETEROCYCLIC COMPOUND AND ORGANIC LIGHT-EMITTING DEVICE INCLUDING THE SAME

CROSS-REFERENCE TO RELATED APPLICATION

Korean Patent Application No. 10-2013-0099919, filed on Aug. 22, 2013, in the Korean Intellectual Property Office, and entitled: "Heterocyclic Compound and Organic Light-Emitting Device Comprising The Same," is incorporated by reference herein in its entirety.

BACKGROUND

1. Field

Embodiments relate to a heterocyclic compound and an organic light-emitting device including the same.

2. Description of the Related Art

Organic light-emitting devices (OLEDs) are self-emitting devices that have advantages such as wide viewing angles, excellent contrast, quick response time, and excellent brightness, driving voltage, and fast response speed characteristics, and may provide multicolored images.

An OLED may have a structure including, e.g., an anode, a hole-transporting layer (HTL), an emission layer (EML), an electron-transporting layer (ETL), and a cathode, which are sequentially stacked on the anode. For example, the HTL, EML, and ETL may be organic thin films formed of organic compounds.

An OLED that has the above-described structure operates as described below.

When voltage is applied between the anode and the cathode, holes injected from the anode may move to the EML via the HTL, and electrons injected from the cathode may move to the EML via the ETL. Carriers (e.g., the holes and the electrons) may recombine in the EML to generate excitons. When the excitons drop from an excited state to a ground state, light is emitted.

SUMMARY

Embodiments are directed to a heterocyclic compound and an organic light-emitting device including the same.

The embodiments may be realized by providing a heterocyclic compound represented by Formula 1 below:

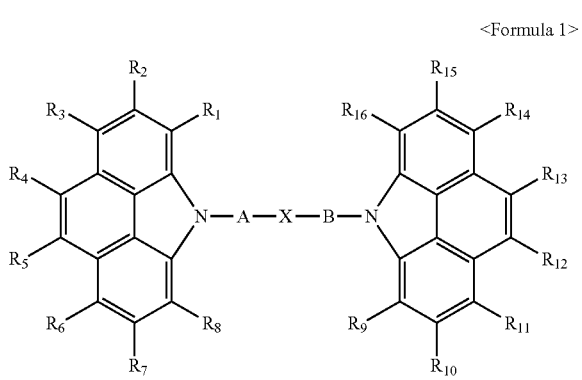

<Formula 1>

In Formula 1, $R_1$ to $R_{16}$ are each independently a hydrogen or a deuterium, X, A, and B are each independently a single bond, a substituted or unsubstituted $C_6$-$C_{60}$ arylene group, a substituted or unsubstituted $C_2$-$C_{60}$ heteroarylene group, and a substituted or unsubstituted $C_6$-$C_{60}$ condensed polycyclic divalent connector, except that X, A, and B are not all simultaneously single bonds.

In Formula 1 above, X, A, and B may be each independently one of a single bond or a group represented by Formulae 2a to 2f below:

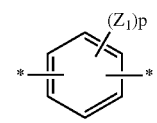

2a

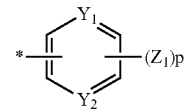

2b

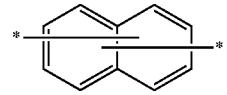

2c

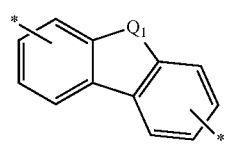

2d

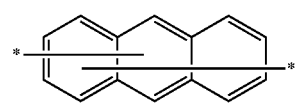

2e

2f wherein, in Formulae 2a to 2f, $Q_1$ may be —$CR_{31}R_{32}$—, —$SiR_{41}R_{42}$—, —O—, —S—, or —$NR_{51}$; $Q_2$ may be O or S; $Y_1$ and $Y_2$ may be each independently CH or N; $R_{31}$, $R_{32}$, $R_{41}$, $R_{42}$, $R_{51}$, and $Z_1$ are each independently a hydrogen, a deuterium, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxy group, or a carboxy group, and, in a case of a plurality of $Z_1$s, each of the $Z_1$s may be the same or are different from each other; p may be an integer of 1 to 4; and * represents a binding site.

$R_{31}$, $R_{32}$, $R_{41}$, $R_{42}$, $R_{51}$ and $Z_1$ of Formulae 2a to 2f may be each independently a hydrogen, a deuterium, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, or a halogen group.

At least one of X, A, or B may be a group represented by Formula 2d, and $Q_1$ of Formula 2d may be —$CR_{31}R_{32}$— or —$NR_{51}$.

$R_1$ to $R_{16}$ in Formula 1 may be hydrogen.

The compound represented by Formula 1 may be one of compounds 1, 8, 18, 28, 39, 46, 56, or 63, below:

The embodiments may be realized by providing an organic light-emitting device including a first electrode; a second electrode; and an organic layer between the first electrode and second electrode, wherein the organic layer includes the compound according to an embodiment.

The organic layer may include an emission layer.

The organic layer may include a green emission layer or a red emission layer.

The organic layer may include an emission layer, and further includes one of an electron-injecting layer, an electron-transporting layer, and a functional layer having both electron injection and electron transporting capabilities, a hole-injecting layer, a hole-transporting layer, or a functional layer having both hole-injecting and hole-transporting capabilities, and the emission layer may include an anthracene-based compound, an arylamine-based compound, or a styryl-based compound.

The organic layer may include an emission layer, and further includes one of an electron-injecting layer, an electron-transporting layer, a functional layer having both electron injecting and electron transporting capabilities, a hole-injecting layer, a hole-transporting layer, or a functional layer having both hole injecting and hole transporting capabilities, and any one layer of a red layer, a green layer, a blue layer, or a white layer of the emission layer may include a phosphorescent compound.

The organic layer may include one of the hole-injecting layer, the hole-transporting layer, or the functional layer having both hole injecting and hole transporting capabilities, and the hole-injecting layer, the hole-transporting layer, or the functional layer having both hole injecting and hole transporting capabilities may include a charge-generating material.

The charge-generating material may be a p-dopant.

The p-dopant may include a quinone derivative.

The p-dopant may include a metal oxide.

The p-dopant may include a cyano group containing compound.

The organic layer may include an electron-transporting layer, the electron-transporting layer including an electron-transporting material and a metal complex.

The metal complex may include lithium quinolate or Compound 203 below:

<Compound 203>

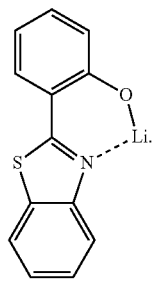

The organic layer including the heterocyclic compound may be formed using a wet process.

The embodiments may be realized by providing a flat display device comprising the organic light-emitting diode according to an embodiment, wherein the first electrode of the organic light-emitting diode is electrically connected to a source electrode or a drain electrode of a thin film transistor.

BRIEF DESCRIPTION OF THE DRAWING

Features will be apparent to those of skill in the art by describing in detail exemplary embodiments with reference to the attached drawing in which:

FIG. 1 illustrates a schematic view of a structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of at least one of the associated listed items. Expressions such as "at least one of," when preceding a list of elements, modify the entire list of elements and do not modify the individual elements of the list.

A compound according to an embodiment may be represented by Formula 1, below.

<Formula 1>

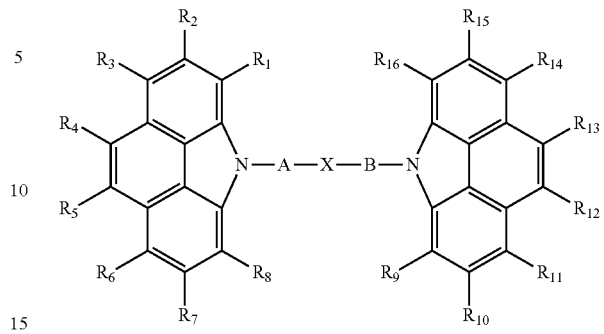

In Formula 1, $R_1$ to $R_{16}$ may each independently be a hydrogen or a deuterium, X, A, and B may each independently be a single bond, a substituted or unsubstituted $C_6$-$C_{60}$ arylene group, a substituted or unsubstituted $C_2$-$C_{60}$ heteroarylene group, and a substituted or unsubstituted $C_6$-$C_{60}$ condensed polycyclic divalent connector. In an implementation, X, A, and B may not all simultaneously be single bonds.

Tris(2-phenylpyridine)iridium (Ir(ppy)$_3$), which is a representative phosphorescent material used in an organic light-emitting device (OLED), emits spectra at CIE 0.30 and 0.63, and the greatest power efficiency at quantum efficiency of 6%. However, such an OLED may have low efficiency, a short lifespan, and low stability. Thus, such an OLED may not be suitable for high efficiency and high quality displays. Accordingly, a phosphorescent material having high efficiency and a long lifespan at low voltage, and an OLED including the phosphorescent material, has been considered.

Compounds represented by Formula 1 and according to an embodiment may function as light-emitting materials for OLEDs. Also, the compounds represented by Formula 1 may have high glass transition temperature (Tg) and high melting point. Accordingly, the OLEDs including a layer prepared using the compound according to an embodiment may have increased heat resistance to Joule heat (that may be generated between organic layers or between an organic layer and a metal electrode), and increased resistance to high temperature environment during electroluminescence. An OLED manufactured by using the heterocyclic compound according to an embodiment may have high durability during maintenance and operation.

Substituents of the compounds of Formula 1 will be described in greater detail.

According to an embodiment, in Formula 1 above, X, A, and B may each independently be a single bond or one of Formulae 2a to 2f, below.

2a

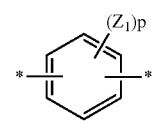

2b

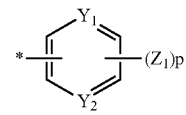

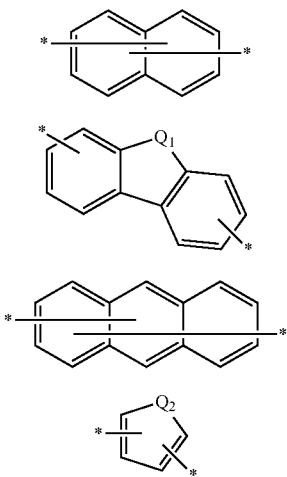

In Formulae 2a to 2f,
Q$_1$ may be —CR$_{31}$R$_{32}$—, —SiR$_{41}$R$_{42}$—, —O—, —S—, or —NR$_{51}$;
Q$_2$ may be O or S;
Y$_1$ and Y$_2$ may each independently be CH or N;
R$_{31}$, R$_{32}$, R$_{41}$, R$_{42}$, R$_{51}$, and Z$_1$ may each independently be a hydrogen, a deuterium, a substituted or unsubstituted C$_1$-C$_{20}$ alkyl group, a substituted or unsubstituted C$_6$-C$_{20}$ aryl group, a substituted or unsubstituted C$_2$-C$_{20}$ heteroaryl group, a substituted or unsubstituted C$_6$-C$_{20}$ condensed polycyclic group, a halogen group, a cyano group, a nitro group, a hydroxy group, or a carboxy group. When there is a plurality of Z$_1$s, each of the Z$_1$s may be the same, or may be different. p may be an integer of 1 to 4; and * represents a binding site or a bond.

In an implementation, in Formula 1 above, R$_1$ to R$_{16}$ may be hydrogen.

In an implementation, in Formulae 2a to 2f above, R$_{31}$, R$_{32}$, R$_{41}$, R$_{42}$, R$_{51}$, and Z$_1$ may be each independently a hydrogen, a deuterium, a substituted or unsubstituted C$_1$-C$_{20}$ alkyl group, a substituted or unsubstituted C$_6$-C$_{20}$ aryl group, a substituted or unsubstituted C$_2$-C$_{20}$ heteroaryl group, a substituted or unsubstituted C$_6$-C$_{20}$ condensed polycyclic group, or a halogen group. For example, at least one of X, A, or B may be a group represented by one of Formulae 2a, 2b, 2d, or 2f, and/or Q$_1$ may be —CR$_{31}$R$_{32}$—, or —NR$_{51}$.

In an implementation, at least one of X, A, or B may be a group represented by Formula 2d, and in Formula 2d, Q$_1$ may be —CR$_{31}$R$_{32}$—, or —NR$_{51}$.

Hereinafter, representative substituents of the substituents used herein are described as follows (carbon numbers limiting the substituents are non-limiting and do not limit the properties of the substituents, and definitions of substituents that are not described in the present specification are the same as conventional definitions).

An unsubstituted C$_1$-C$_{60}$ alkyl group may have a linear or a branched form, and non-limiting examples of the unsubstituted C$_1$-C$_{60}$ alkyl group include methyl, ethyl, propyl, isobutyl, sec-butyl, pentyl, iso-amyl, hexyl, heptyl, octyl, nonyl, dodecyl, and the like. When substituted, at least hydrogen atom of the C$_1$-C$_{60}$ alkyl group may be substituted with a deuterium atom, a halogen atom, a hydroxy group, a nitro group, a cyano group, an amino group, an amidino group, a hydrazine group, a hydrazone group, a carboxylic acid group or a salt thereof, a sulfonic acid group or a salt thereof, phosphoric acid or a salt thereof, or a C$_1$-C$_{10}$ alkyl group, a C$_1$-C$_{10}$ alkoxy group, a C$_2$-C$_{10}$ alkenyl group, a C$_2$-C$_{10}$ alkynyl group, a C$_6$-C$_{16}$ aryl group, or a C$_2$-C$_{16}$ heteroaryl group.

An unsubstituted C$_2$-C$_{60}$ alkenyl group is a C$_2$-C$_{60}$ alkyl group having at least one carbon-carbon double bond in the center or at a terminal of the unsubstituted C$_2$-C$_{60}$ alkyl group. Examples of the unsubstituted C$_2$-C$_{60}$ alkenyl group are ethenyl, propenyl, and butenyl. When substituted, at least one hydrogen atom of the C$_2$-C$_{60}$ alkenyl group may be substituted with the substituents described above in conjunction with the substituted C$_1$-C$_{60}$ alkyl group.

The unsubstituted C$_2$-C$_{60}$ alkynyl group is a C$_2$-C$_{60}$ alkyl group having at least one carbon-carbon triple bond in the center or at a terminal thereof. Examples of the unsubstituted C$_2$-C$_{60}$ alkynyl group are acetylene, propyne, phenyl acetylene, isopropyl acetylene, t-butyl acetylene, and diphenyl acetylene. When substituted, at least one hydrogen atom of the C$_2$-C$_{60}$ alkynyl group may be substituted with the substituents described above in conjunction with the substituted C$_1$-C$_{60}$ alkyl group.

The unsubstituted C$_3$-C$_{60}$ cycloalkyl group represents a ring form C$_3$-C$_{60}$ alkyl group. When substituted, at least one hydrogen atom of the cycloalkyl group may be substituted with the substituents described above in conjunction with the substituted C$_1$-C$_{60}$ alkyl group.

The unsubstituted C$_1$-C$_{60}$ alkoxy group is a group having a structure of —OA (wherein, A is the unsubstituted C$_1$-C$_{60}$ alkyl group as described above), and non-limiting examples of the alkoxy group are methoxy, ethoxy, propoxy, isopropyloxy, butoxy, and pentoxy. When substituted, at least one hydrogen atom of the alkoxy group may be substituted with the substituents described above in conjunction with the substituted C$_1$-C$_{60}$ alkyl group.

The unsubstituted C$_6$-C$_{60}$ aryl group represents a carbocyclic aromatic system having at least one ring, and when there are two or more rings, the two or more rings may be fused or connected to each other via a single bond. The term "aryl" as used herein includes aromatic systems such as phenyl, naphthyl, and anthracenyl. When substituted, at least one hydrogen atom of the aryl group may be substituted with the substituents described above in conjunction with the substituted C$_1$-C$_{60}$ alkyl group.

Examples of a substituted or unsubstituted C$_6$-C$_{60}$ aryl group include a phenyl group, a C$_1$-C$_{10}$ alkylphenyl group (for example, an ethylphenyl group), a biphenyl group, a C$_1$-C$_{10}$ alkyl biphenyl group, a C$_1$-C$_{10}$ alkoxy biphenyl group, an o-, m-, and p-tolyl group, an o-, m-, and p-cumenyl group, a mesityl group, a phenoxy phenyl group, an (α,α-dimethyl benzene) phenyl group, an (N,N'-dimethyl) aminophenyl group, an (N,N'-diphenyl) aminophenyl group, a pentalenyl group, an indenyl group, a naphthyl group, a C$_1$-C$_{10}$ alkyl naphthyl group (for example, a methyl naphthyl group), a C$_1$-C$_{10}$ alkoxy naphthyl group (for example, a methoxy naphthyl group), an anthracenyl group, an azulenyl group, an acenaphthylenyl group, a phenalenyl group, a fluorenyl group, an anthraquinolyl group, a methyl anthryl group, a phenanthryl group, a triphenylene group, a pyrenyl group, a chrysenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, and an ovalenyl group.

The unsubstituted $C_2$-$C_{60}$ heteroaryl group may include 1, 2, 3, or 4 heteroatoms selected from among N, O, P, and S, and when there are two or more rings, the two or more rings may be fused or connected to each other via a single bond. Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. When substituted, at least one hydrogen atom of the heteroaryl group may be substituted with the substituents described above in conjunction with the substituted $C_1$-$C_{60}$ alkyl group.

The unsubstituted $C_6$-$C_{60}$ aryloxy group is a group represented by —$OA_1$, wherein $A_1$ is the $C_6$-$C_{60}$ aryl group. Examples of the unsubstituted $C_6$-$C_{60}$ aryloxy group include a phenoxy group. When substituted, at least one hydrogen atom of the aryloxy group may be substituted with the substituents described above in conjunction with the substituted $C_1$-$C_{60}$ alkyl group.

The unsubstituted $C_6$-$C_{60}$ arylthio group is a group represented by —$SA_1$, wherein $A_1$ is the $C_6$-$C_{60}$ aryl group. Examples of the arylthio group include a benzenethio group and a naphthylthio group. When substituted, at least one hydrogen atom of the arylthio group may be substituted with the substituents described above in conjunction with the substituted $C_1$-$C_{60}$ alkyl group.

The unsubstituted $C_6$-$C_{60}$ condensed polycyclic group refers to substituents including two or more rings in which at least one aromatic ring and/or at least one non-aromatic ring are fused together or substituents including unsaturated groups in the ring but are incapable of having a conjugated structure. Thus, the unsubstituted $C_6$-$C_{60}$ condensed polycyclic group is distinguished from an aryl group or a heteroaryl group in that the unsubstituted $C_6$-$C_{60}$ condensed polycyclic group does not have an overall aromaticity.

The compound represented by Formula 1, according to an embodiment, may include one of the following compounds 1-65.

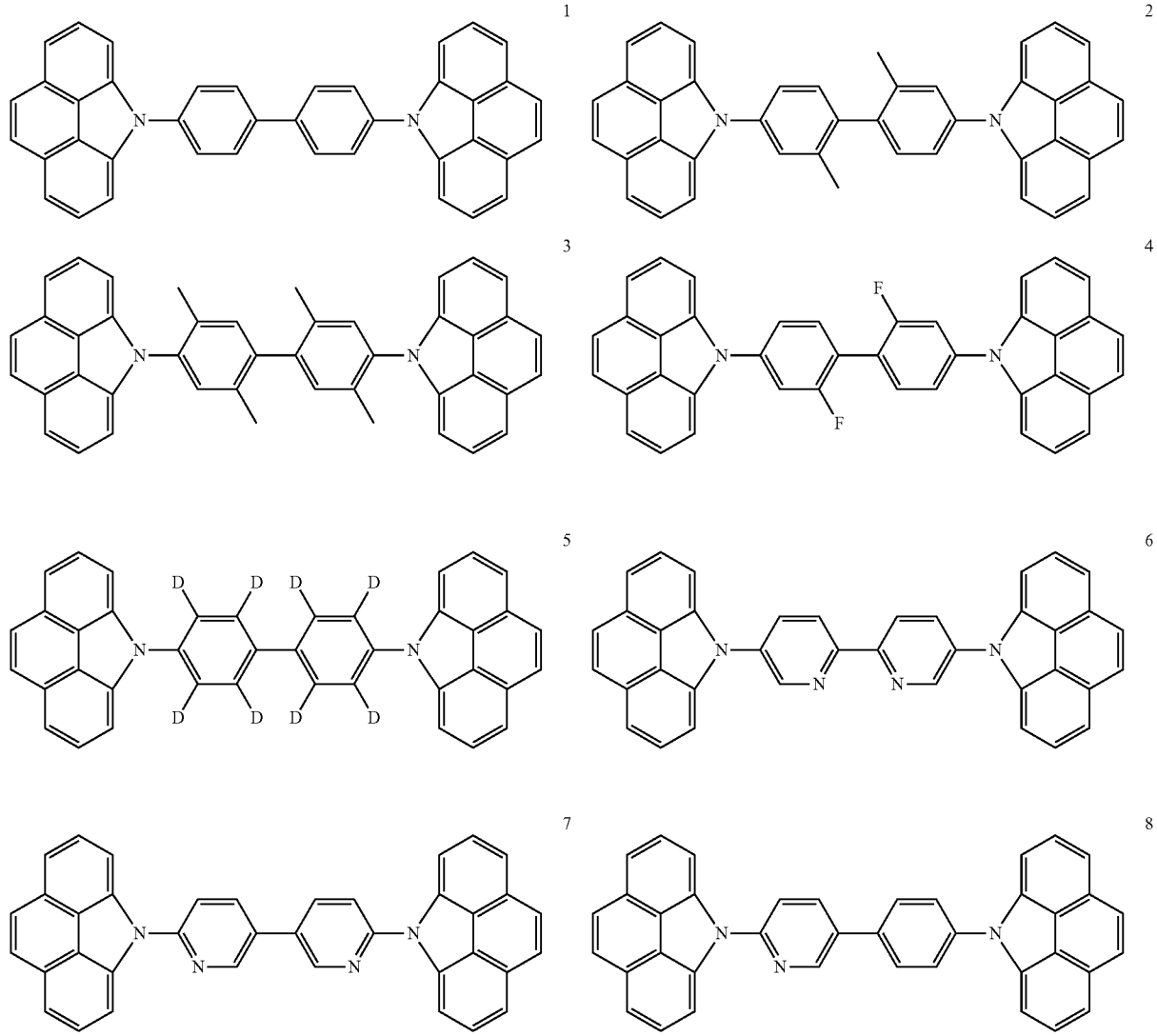

-continued
9
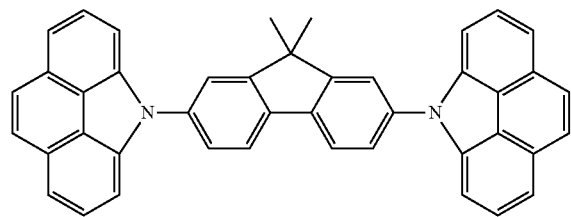
10
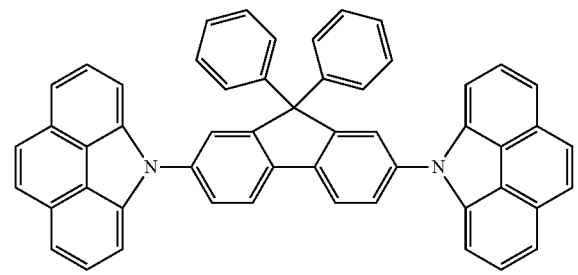
11
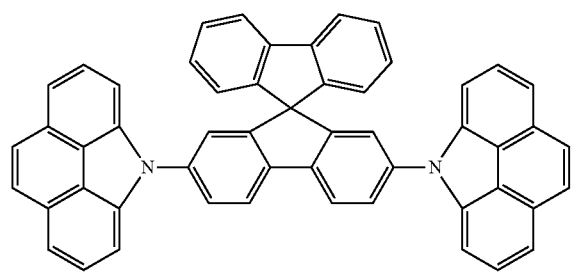
12
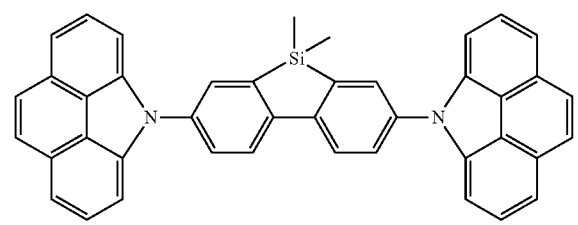
13
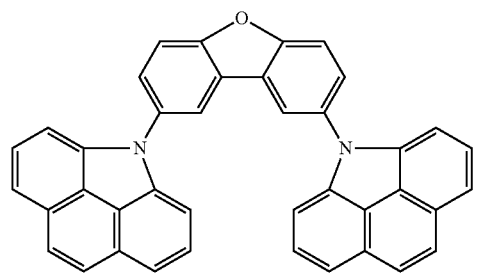
14
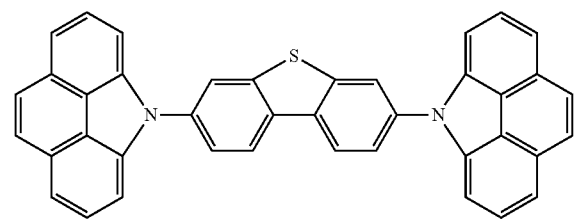
15
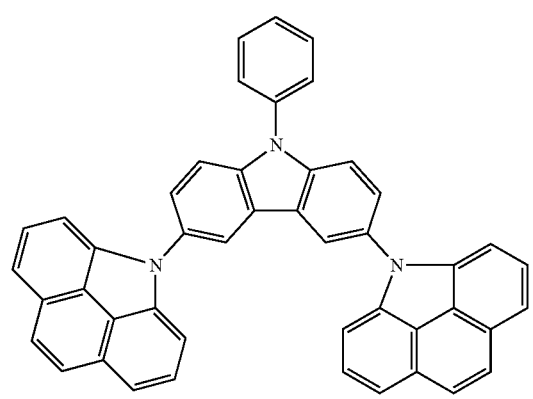
16
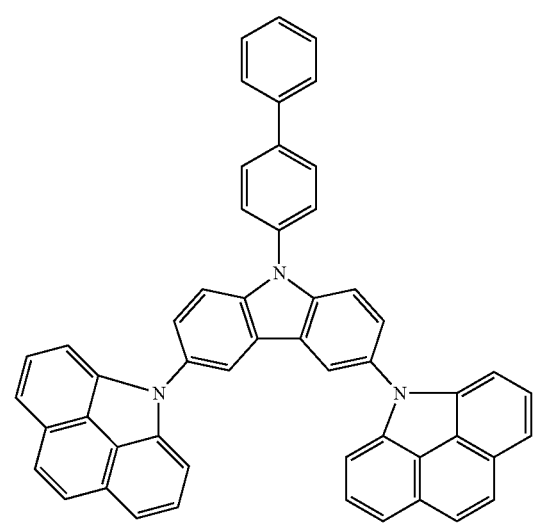

-continued
17
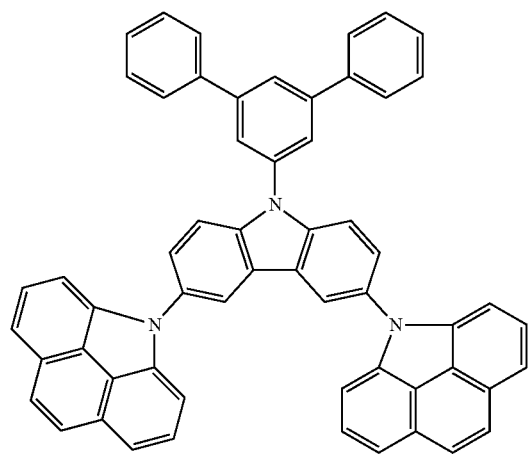
18
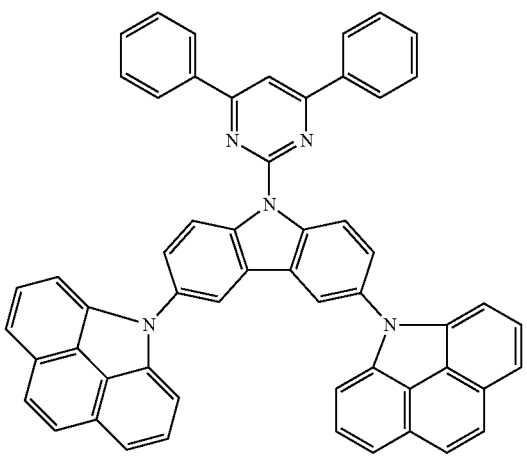
19
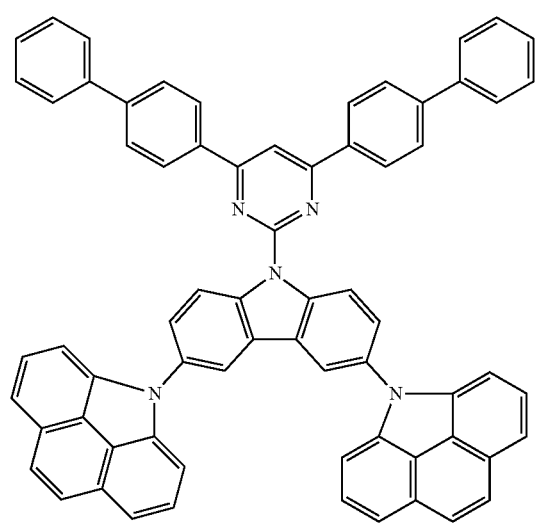
20
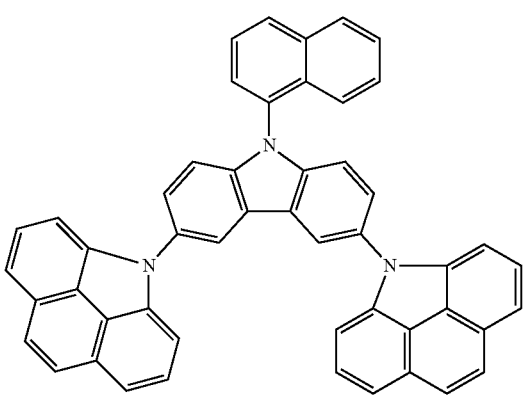
21
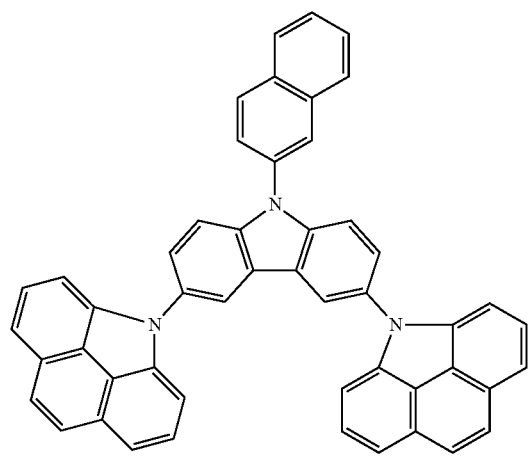
22
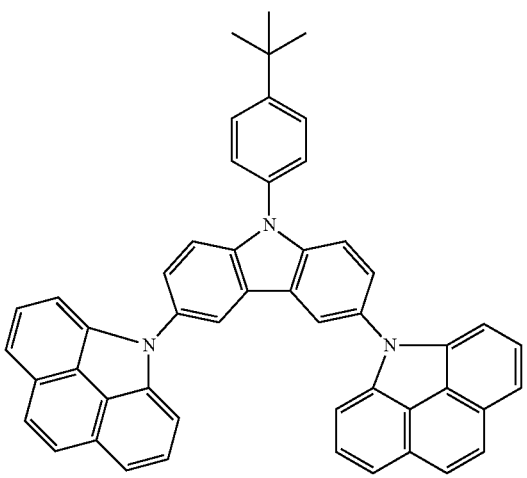

-continued
23
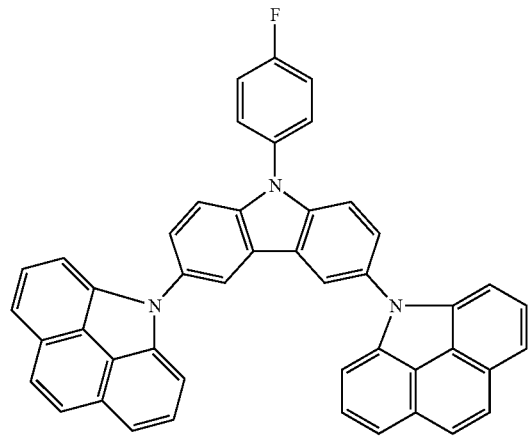
24
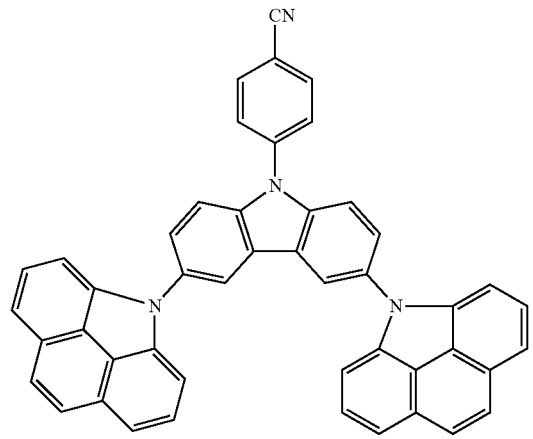
25
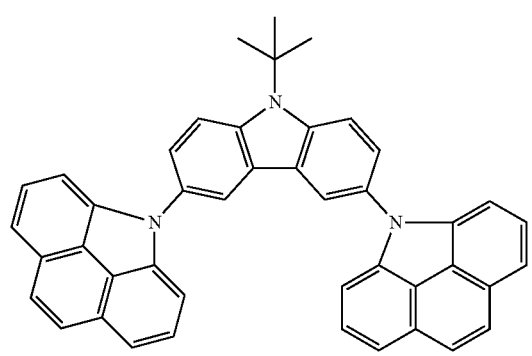
26
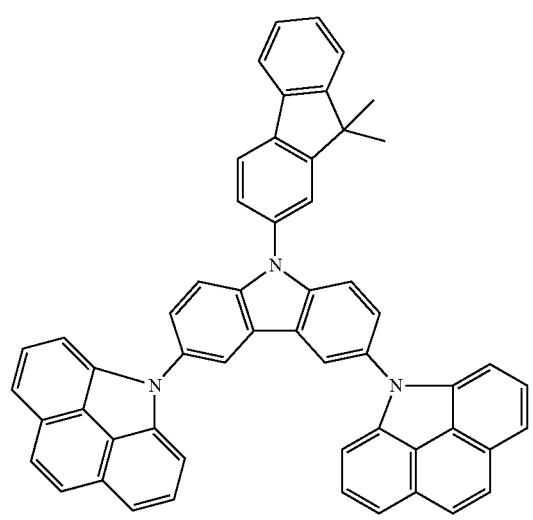
27
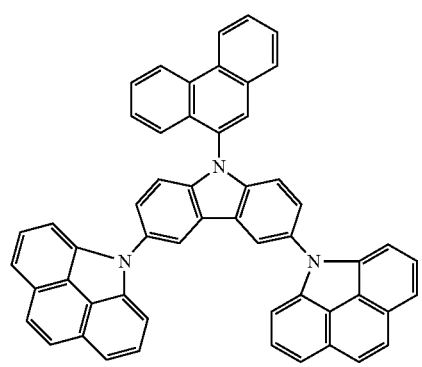
28
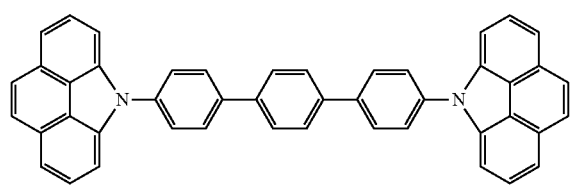
29
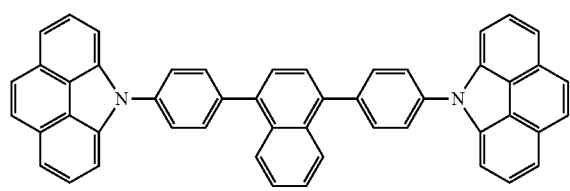
30
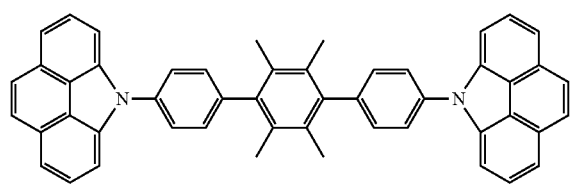

-continued
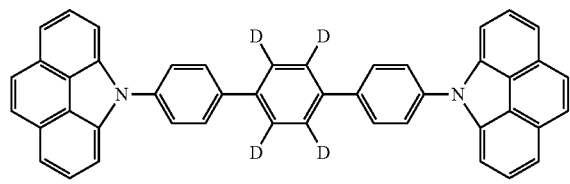
31
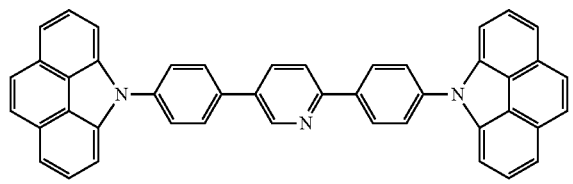
32
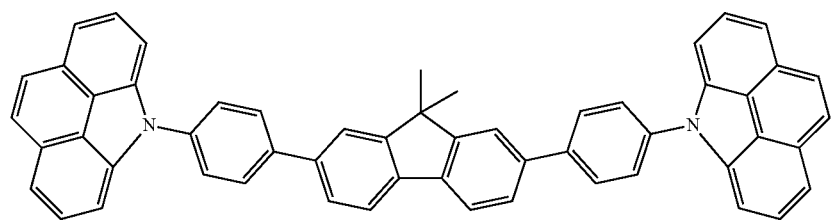
33
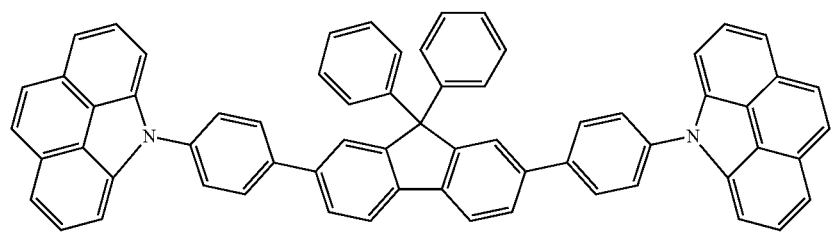
34
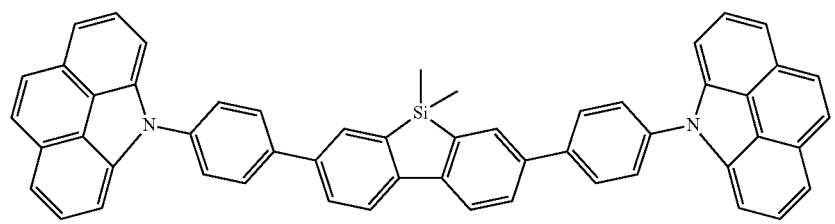
35
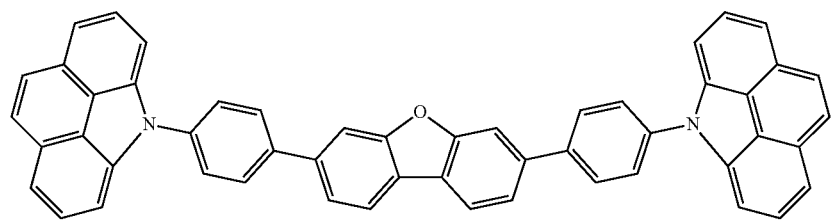
36
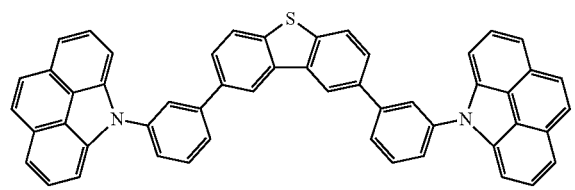
37
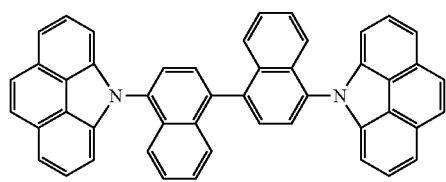
38
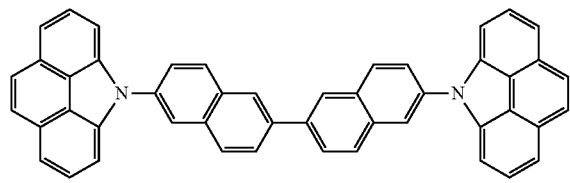
39

-continued
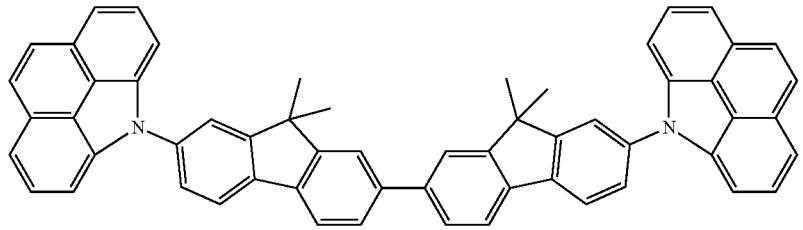
40
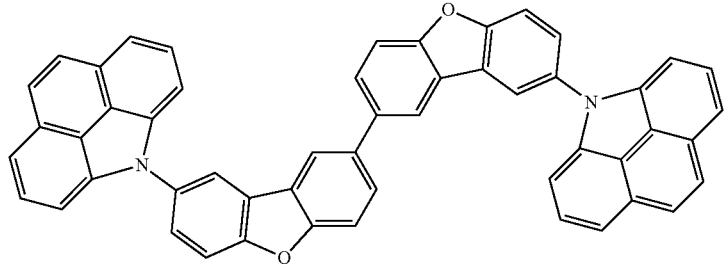
41
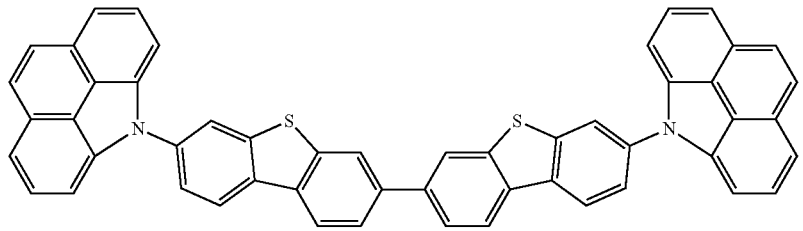
42
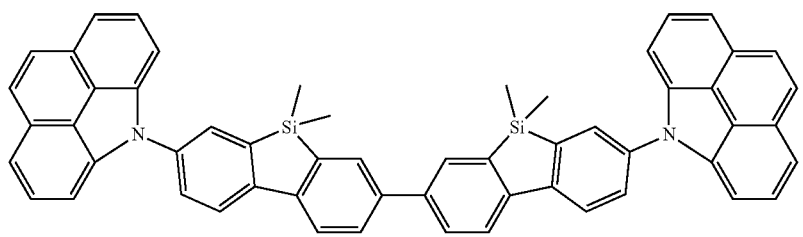
43
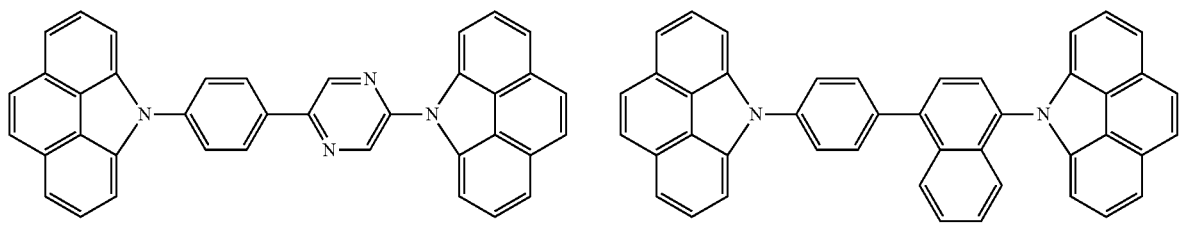
44  45
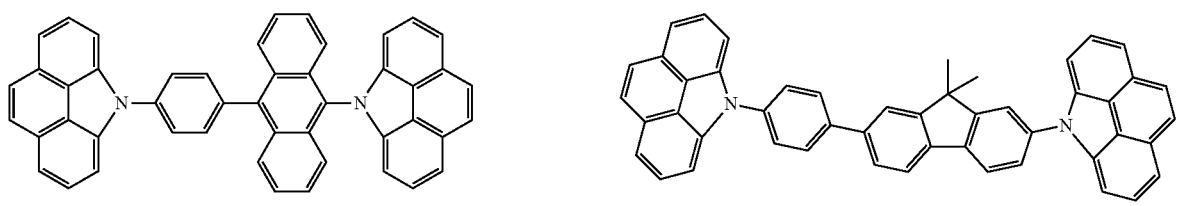
46  47

48
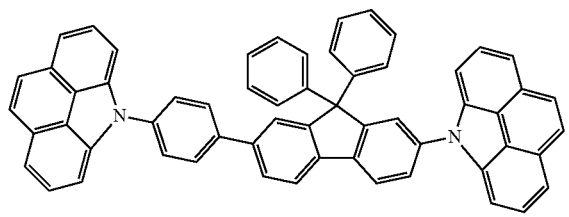
49
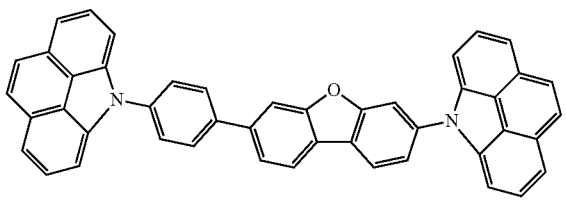
50
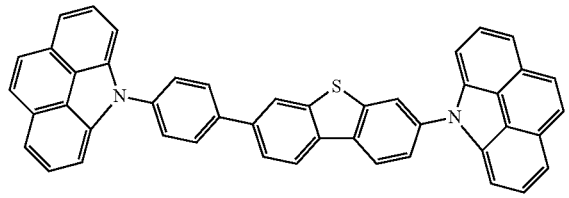
51
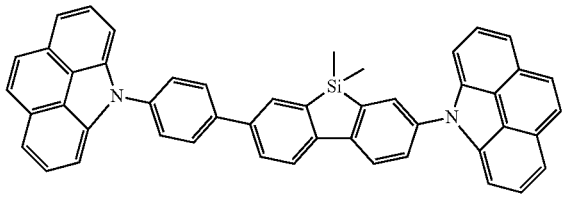
52
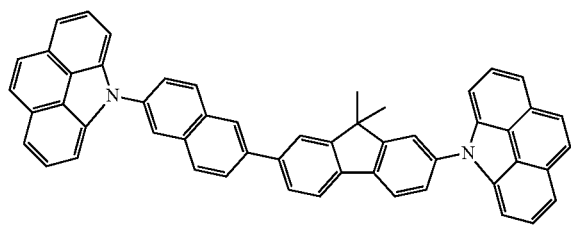
53
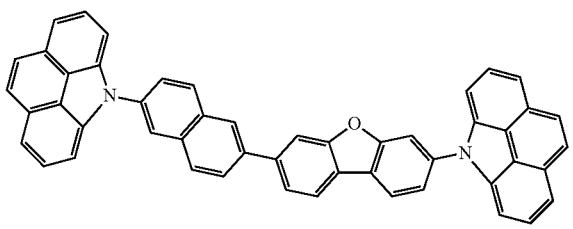
54
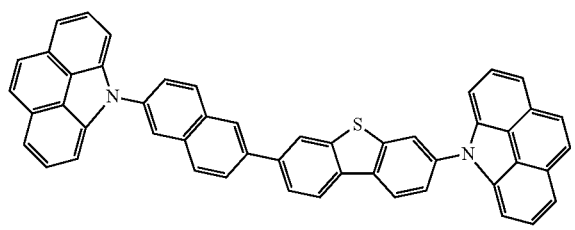
55
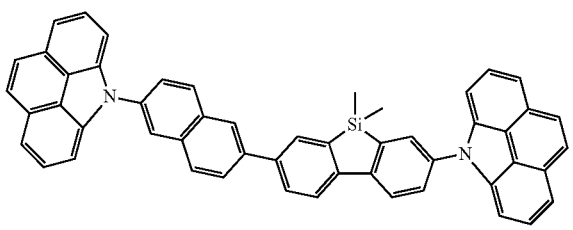
56
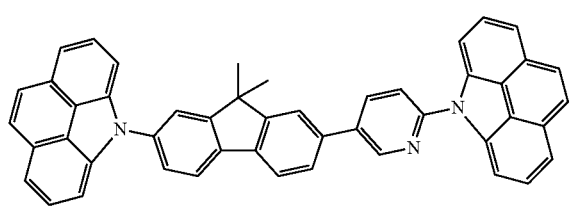
57
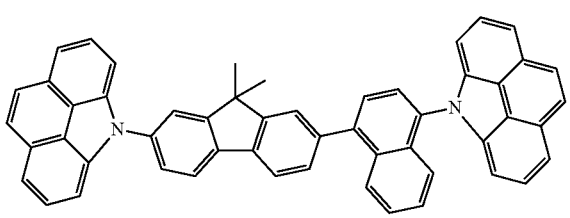
58
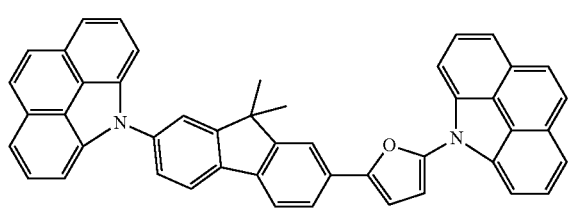
59
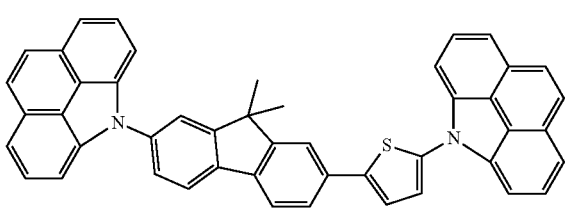

-continued
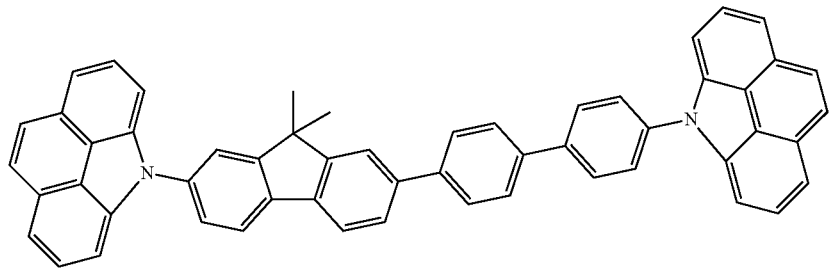
60
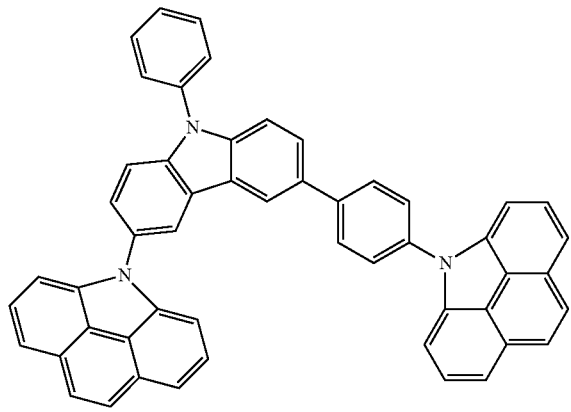
61
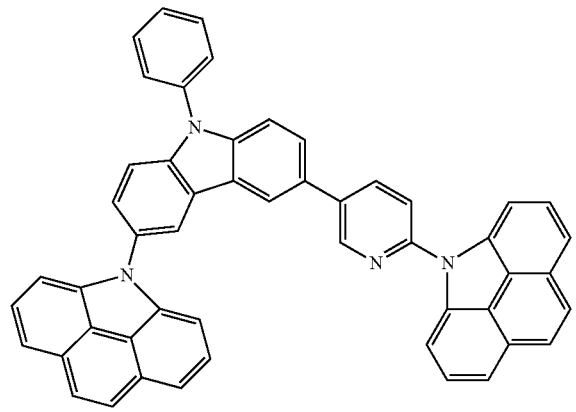
62
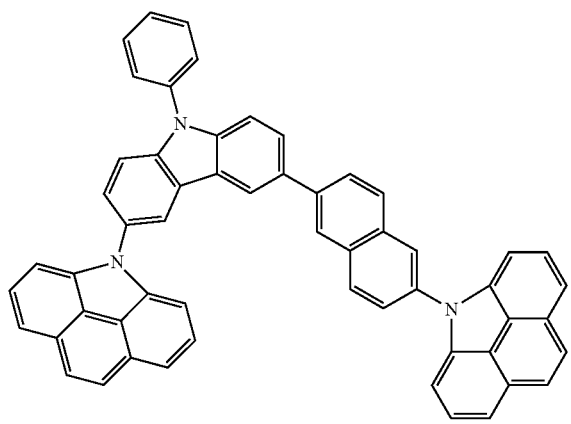
63
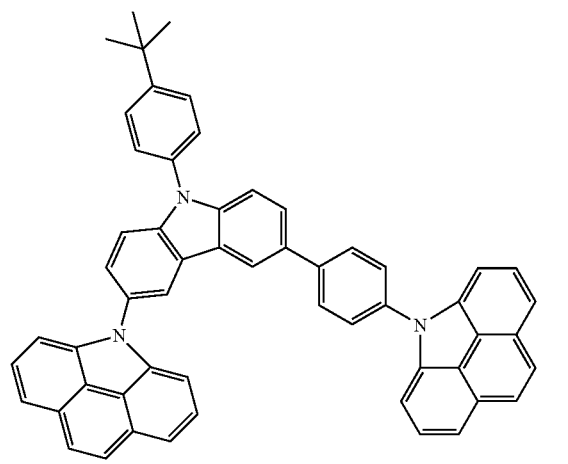
64
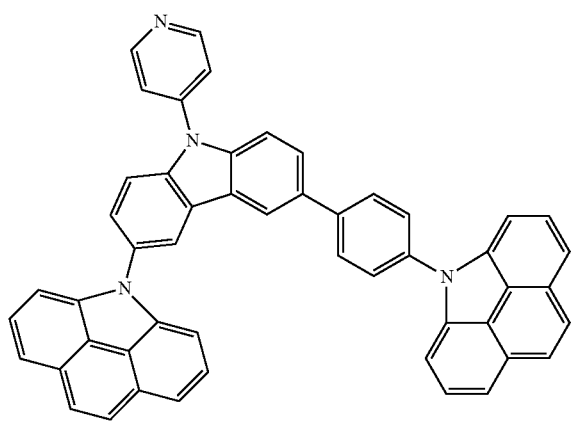
65

An organic light-emitting diode according to an embodiment may include a first electrode; a second electrode; and an organic layer between the first electrode and the second electrode. The organic layer may include a compound represented by Formula 1, above.

The organic layer may include at least one layer selected from a hole-injecting layer (HIL), a hole-transporting layer (HTL), a functional layer having both hole injecting and hole transporting capabilities (hereinafter, "H-functional layer"), a buffer layer, an electron-blocking layer (EBL), an emission layer (EML), a hole-blocking layer (HBL), an electron-transporting layer (ETL), an electron-injecting layer (EIL), and a functional layer having both electron injecting and electron transporting capabilities (hereinafter, "E-functional layer").

For example, the organic layer may include the emission layer. For example, the emission layer may be a green emission layer or a red emission layer.

According to an embodiment, the organic layer may include, e.g., an EIL, an ETL, an EML, an HIL, an HTL, or an H-functional layer. The EML may include an anthracene-based compound, an arylamine-based compound, or a styryl-based compound.

In an implementation, the organic layer may include, e.g., an EIL, an ETL, an EML, an HIL, an HTL, or an H-functional layer. Any one layer of a red layer, a green layer, a blue layer, and a white layer of the EML may include a phosphorescent compound. The HIL, the HTL, or the H-functional layer may include a charge-generating material. The charge-generating material may be a p-dopant. The p-dopant may include, e.g., a quinone derivative, a metal oxide, or a cyano group containing compound.

In an implementation, the organic layer may include an ETL, and the ETL may include, e.g., an electron transporting organic compound and a metal complex. The metal complex may include, e.g., a Li complex.

As used herein, the term "organic layer" refers to a single layer and/or a plurality of layers disposed between the first electrode and the second electrode.

The organic layer includes an EML, and the EML may include the compound according to an embodiment. In an implementation, the organic layer may include at least one of an HIL, an HTL, an H-functional layer, and at least one of the HIL, the HTL, and the H-functional layer may include the compound according to an embodiment.

FIG. 1 illustrates a schematic view of a structure of an organic light-emitting diode according to an embodiment. Hereinafter, a structure and a method of manufacturing an organic light-emitting diode according to an embodiment will be described with reference to FIG. 1 as follows:

A substrate (not shown) may be a suitable substrate that is used for organic light-emitting diodes. In an implementation, the substrate may be a glass substrate or a transparent plastic substrate with strong mechanical strength, thermal stability, transparency, surface smoothness, ease of handling, and water resistance.

A first electrode may be formed by depositing or sputtering a first electrode-forming material onto a surface of the substrate. When the first electrode is an anode, a material having a high work function may be used as the first electrode-forming material to facilitate hole injection. The first electrode may be a reflective electrode or a transmission electrode. Transparent and conductive materials, such as ITO, IZO, SnO$_2$, and ZnO, may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single layer structure or a multi-layer structure including at least two layers. For example, the first electrode may have a three-layered structure of ITO/Ag/ITO, but it is not limited thereto.

An organic layer may be disposed on the first electrode.

The organic layer may include a hole-injecting layer (HIL), a hole-transporting layer (HTL), a buffer layer (not shown), an emission layer (EML), an electron-transporting layer (ETL), or an electron-injecting layer (EIL).

The HIL may be formed on the first electrode by various methods, such as vacuum deposition, spin coating, casting, or Langmuir-Blodgett (LB) deposition.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about 10$^{-8}$ torr to about 10$^{-3}$ torr, and a deposition rate of about 0.01 Å/sec to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in a range of about 2000 rpm to about 5000 rpm, and a temperature at which heat treatment is performed to remove a solvent after coating may be in a range of about 80° C. to about 200° C. However, the coating conditions are not limited thereto.

The HIL may be formed of any known hole-injecting material. Non-limiting examples of the hole-injecting material are N,N'-diphenyl-N,N'-bis-[4-(phenyl-m-tolyl-amino)-phenyl]-biphenyl-4,4'-diamine, (DNTPD); a phthalocyanine compound such as copper phthalocyanine; 4,4',4''-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and (polyaniline)/poly(4-styrenesulfonate) (PANI/PSS):

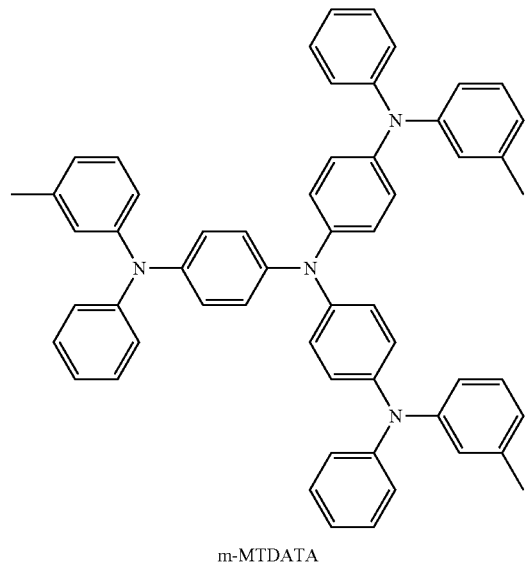

m-MTDATA

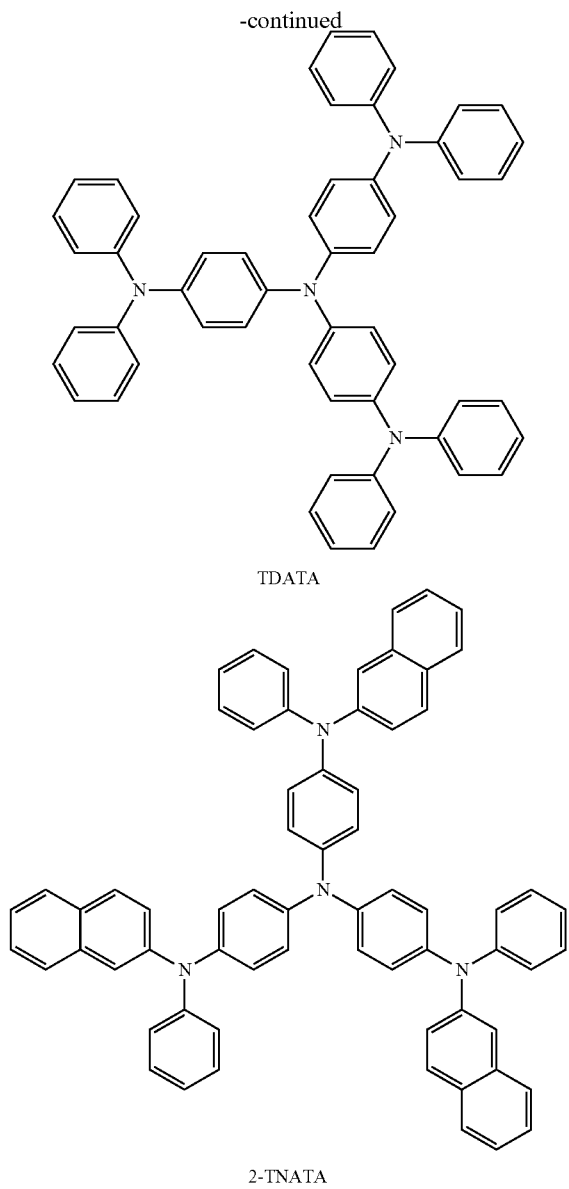

TDATA

2-TNATA

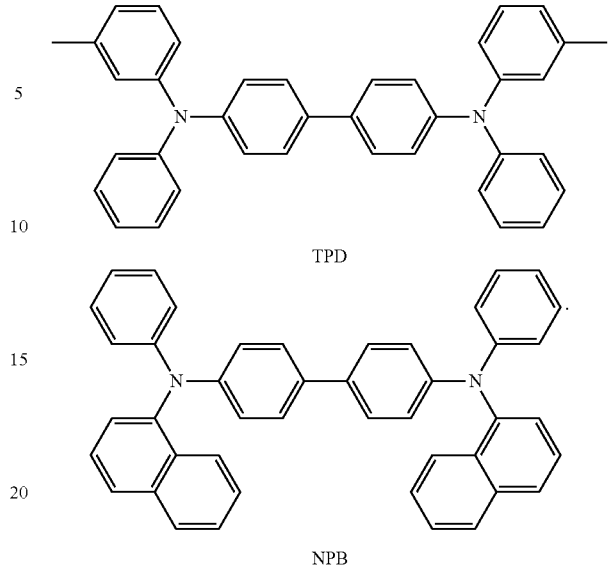

TPD

NPB

The thickness of the HTL may be about 50 Å to about 2000 Å, e.g., about 100 Å to about 1500 Å. When the thickness of the HTL is within these ranges, the HTL may have good hole-transporting ability without a substantial increase in driving voltage.

The H-functional layer (having both hole injecting and hole transporting capabilities) may contain one or more materials from each group of the HIL materials and HTL materials. The thickness of the H-functional layer may be about 500 Å to about 10,000 Å, e.g., about 100 Å to about 1,000 Å. When the thickness of the H-functional layer is within these ranges, the H-functional layer may have good hole injecting and transporting capabilities without a substantial increase in driving voltage.

At least one of the HIL, HTL, and H-functional layer may include at least one of compounds represented by Formula 300 below and compounds represented by Formula 350 below:

<Formula 300>

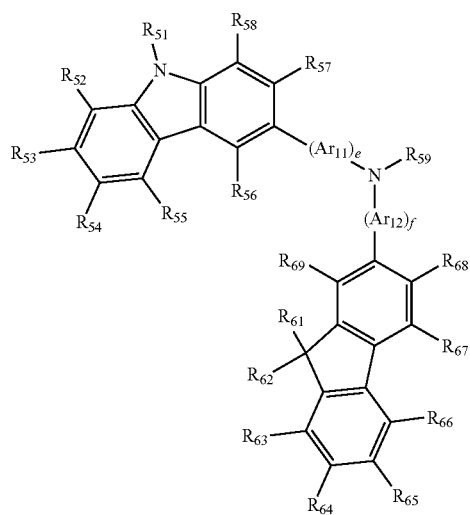

The thickness of the HIL may be about 100 Å to about 10000 Å, e.g., about 100 Å to about 1000 Å. When the thickness of the HIL is within these ranges, the HIL may have good hole-injecting ability without a substantial increase in driving voltage.

Then, the HTL may be formed on the HIL by using vacuum deposition, spin coating, casting, LB deposition, or the like. When the HTL is formed using vacuum deposition or spin coating, the conditions for deposition and coating may be similar to those for the formation of the HIL, though the conditions for the deposition and coating may vary according to the material that is used to form the HTL.

Suitable hole-transporting materials may be used as the hole-transporting material. Non-limiting examples of hole-transporting material may include carbazole derivatives, such as N-phenylcarbazole and polyvinylcarbazole; N,N'-bis(3-methylphenyl)-N,N'-diphenyl-[1,1-biphenyl]-4,4'-di-amine (TPD), 4,4',4"-tris(N-carbazolyl)triphenylamine (TCTA), and N,N'-di(1-naphthyl-N,N'-diphenylbenzidine) (NPB).

<Formula 350>

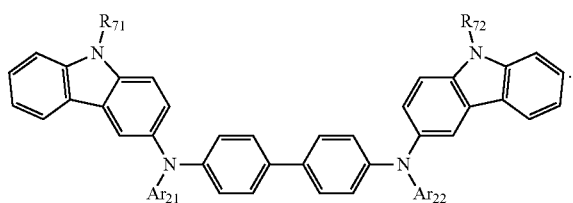

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer of 0 to 5, or 0, 1, or 2. For example, e may be 1 and f may be 0, but they are not limited thereto.

In Formulae 300 and 350 above, $R_{51}$ to $R_{58}$, $R_{61}$ to $R_{69}$, and $R_{71}$ and $R_{72}$ may be each independently a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, and $R_{71}$ and $R_{72}$ may be each independently one of a hydrogen; a deuterium; a halogen atom; a hydroxyl group; a cyano group; a nitro group; an amino group; an amidino group; a hydrazine group; a hydrazone group; a carboxylic acid group or a salt thereof; a sulfonic acid group or a salt thereof; phosphoric acid or a salt thereof; a $C_1$-$C_{10}$ alkyl group (for example, a methyl group, an ethyl group, a propyl group, a butyl group, a pentyl group, and a hexyl group); a $C_1$-$C_{10}$ alkoxy group (for example, a methoxy group, an ethoxy group, a propoxy group, a butoxy group, and a pentoxy group); a $C_1$-$C_{10}$ alkyl group and a $C_1$-$C_{10}$ alkoxy group, each substituted with at least one of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof; and phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group each substituted with at least one of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, phosphoric acid or a salt thereof, a $C_1$-$C_{10}$ alkyl group, and a $C_1$-$C_{10}$ alkoxy group, but they are not limited thereto.

In Formula 300, $R_{59}$ may be one of a phenyl group; a naphthyl group; an anthryl group; a biphenyl group; a pyridyl group; and a phenyl group, a naphthyl group, an anthryl group, a biphenyl group, and a pyridyl group, each substituted with at least one of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, phosphoric acid or a salt thereof, a substituted or unsubstituted $C_1$-$C_{20}$ alkyl group, and a substituted or unsubstituted $C_1$-$C_{20}$ alkoxy group.

According to an embodiment, a compound represented by Formula 300 above may be represented by Formula 300A below, but it is not limited thereto:

<Formula 300A>

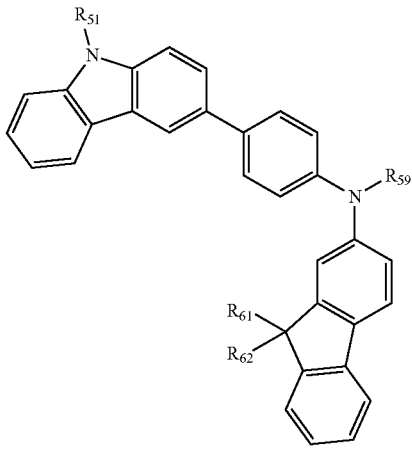

In Formula 300A, detailed descriptions of $R_{51}$, $R_{61}$, $R_{62}$, and $R_{59}$ are the same as described above.

For example, at least one of the HIL, HTL, and H-functional layer may include at least one of compounds 301 to 320 below, but it is not limited thereto:

301

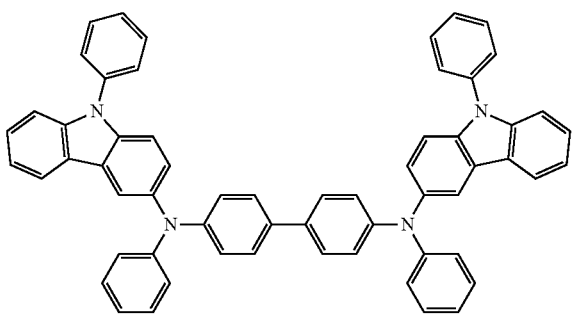

302

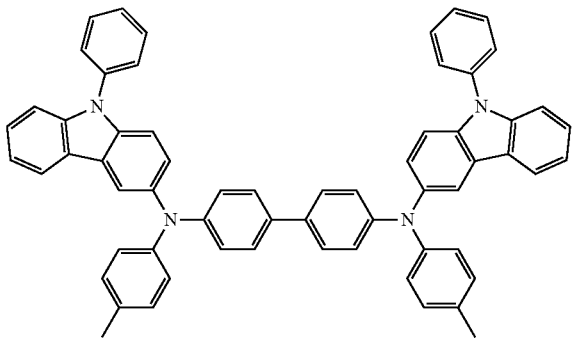

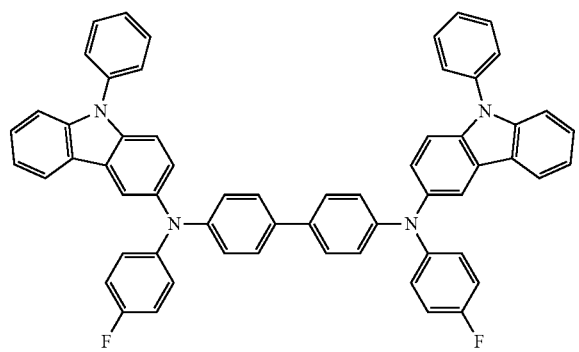
303
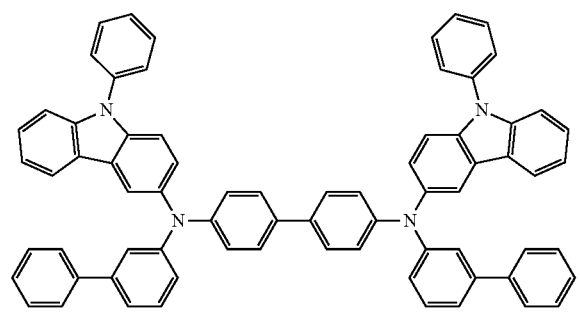
307
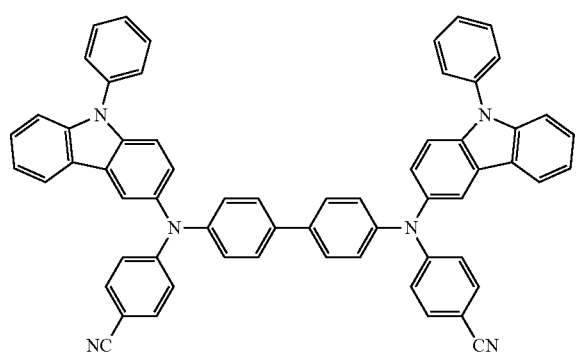
304
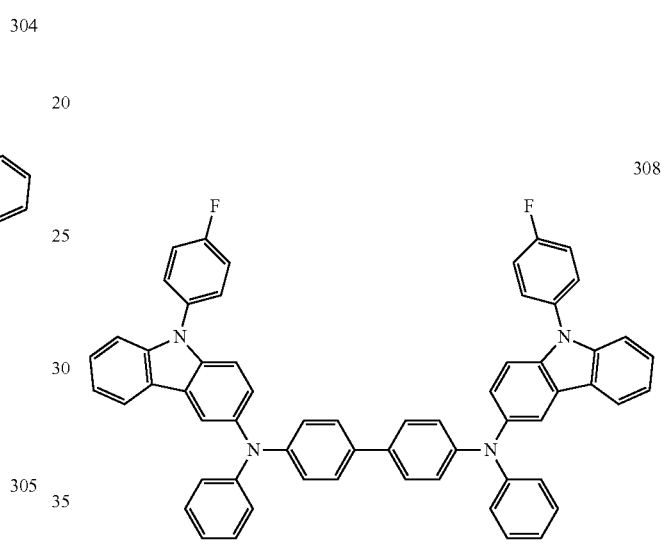
308
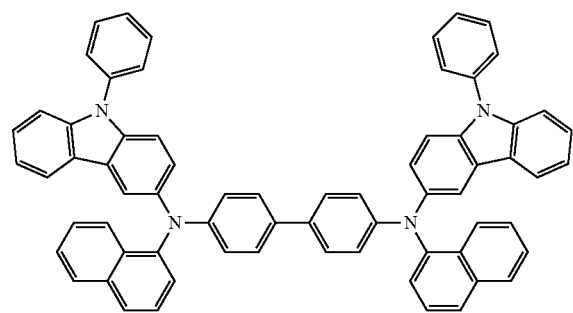
305
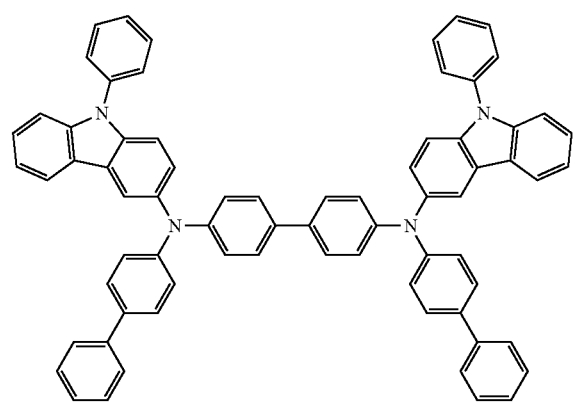
306
309

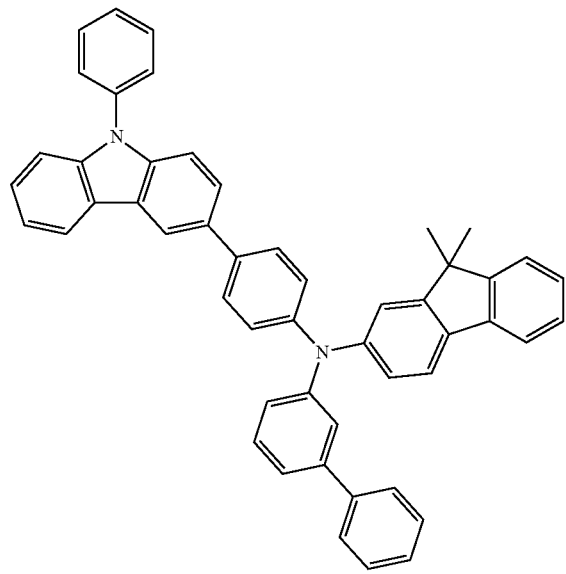
310
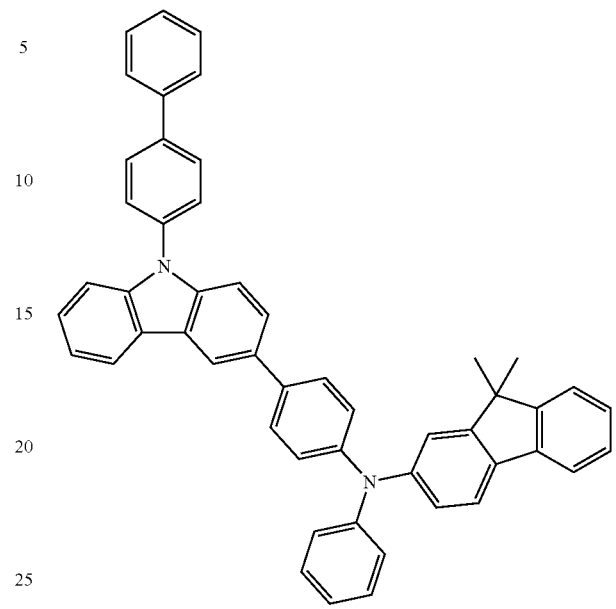
312
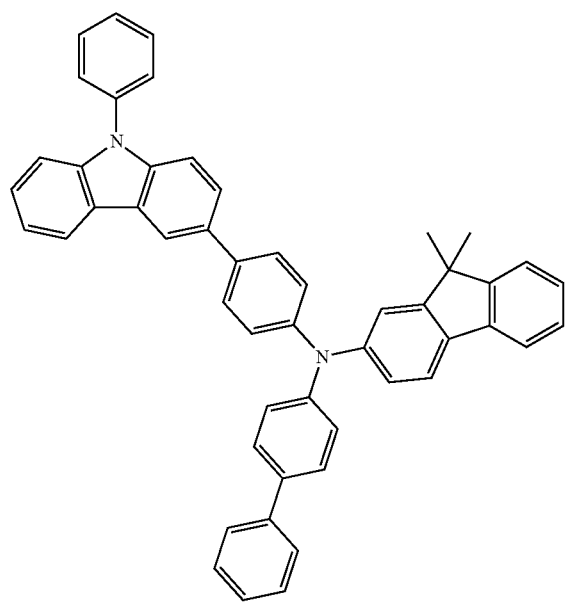
311
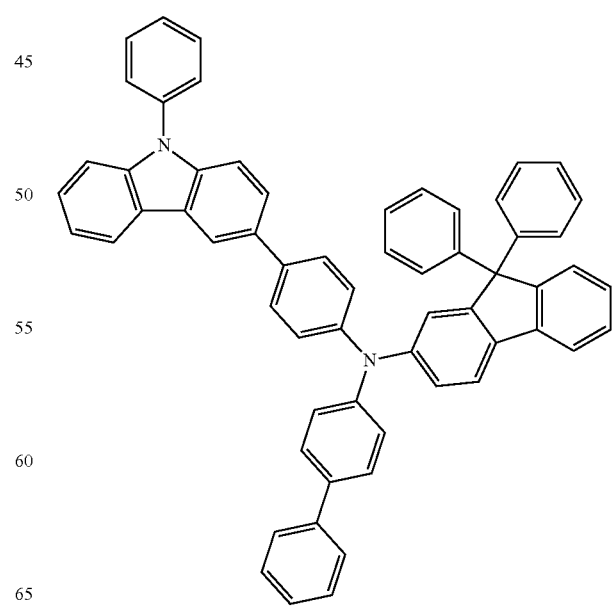
313

314
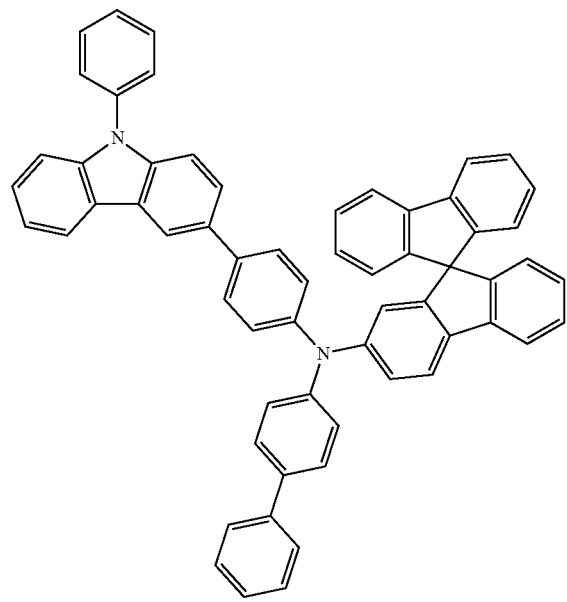
316
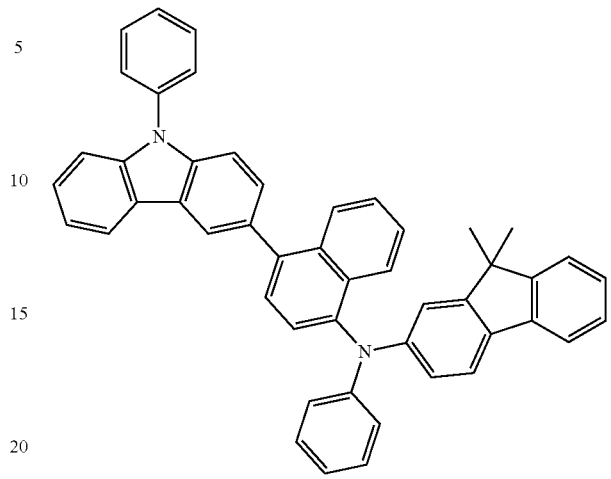
315
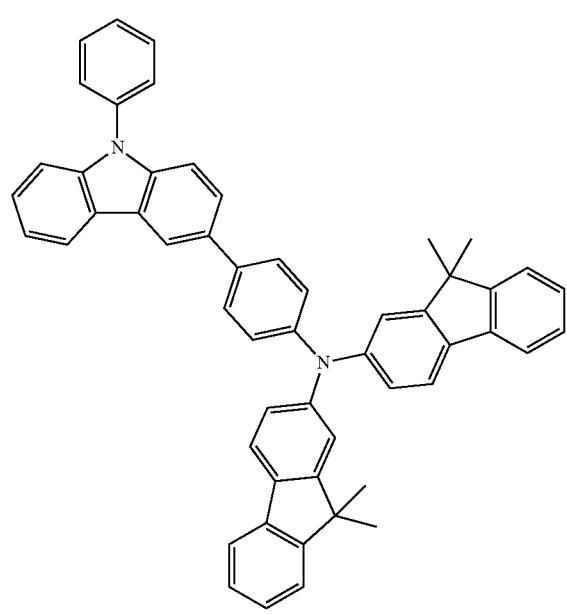
317
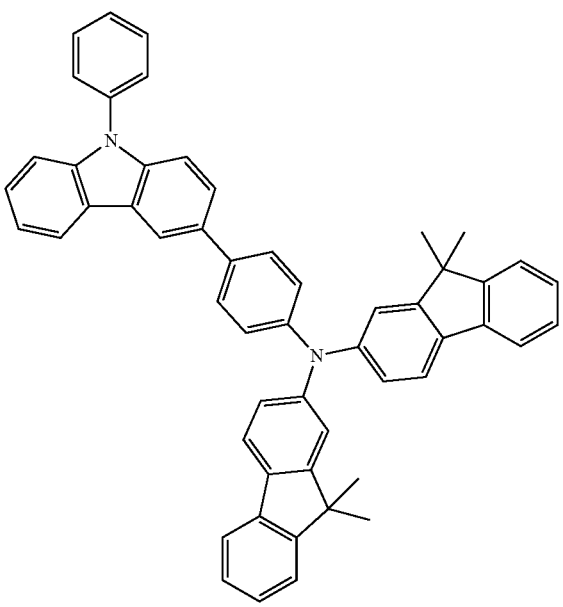

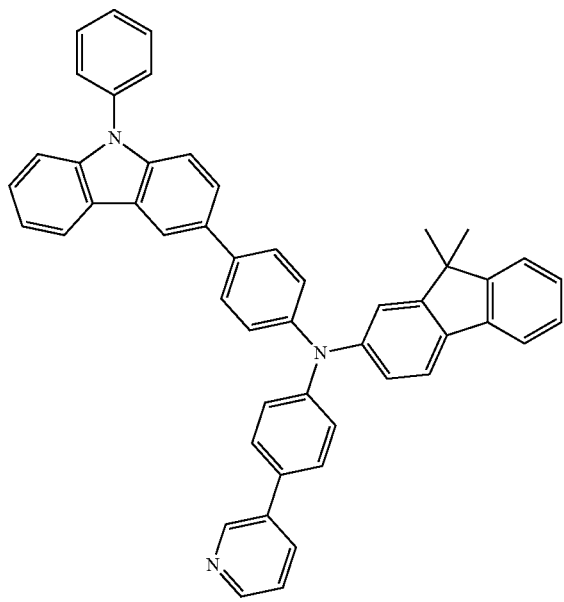

318

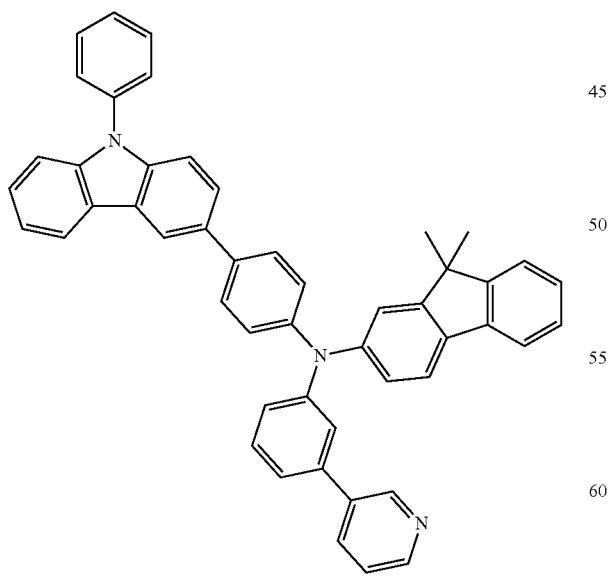

319

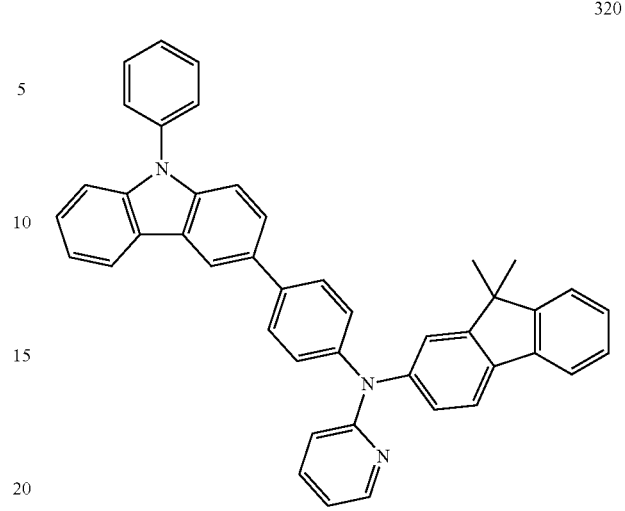

320

At least one of the HIL, HTL, and H-functional layer may further include a charge-generating material in addition to a suitable hole-transporting material and/or a suitable material having both hole injecting and hole transporting capabilities to help improve conductivity of a film and the like.

The charge-generating material may be, e.g., a p-dopant. The p-dopant may include, e.g., one of a quinone derivative, a metal oxide, or a cyano group containing compound, but it is not limited thereto. Non-limiting examples of the charge-generating material may include quinone derivatives such as tetracyanoquinonedimethane (TCNQ), 2,3,5,6-tetrafluoro-tetracyano-1,4-benzoquinonedimethane (F4-TCNQ), and the like; metal oxides, such as tungsten oxide, molybdenum oxide; and cyano-containing compounds, such as Compound 200 below.

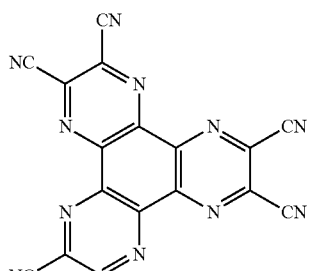

<Compound 200>

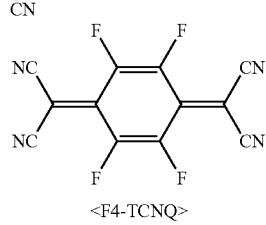

<F4-TCNQ>

When the HIL, the HTL, or the H-functional layer further include a charge-generating material, the charge-generating material may be variously changed such as homogeneously dispersed or heterogeneously distributed in the H-functional layer.

A buffer layer may be interposed between at least one of the HIL, HTL, and H-functional layer, and the EML. The buffer layer may help compensate for an optical resonance distance of light according to a wavelength of the light emitted from the EML, and thus may help increase efficiency of an OLED. The buffer layer may include a suitable hole-injecting material or hole-transporting material. In an implementation, the buffer layer may include a same material as one of the materials included in the HIL, HTL, and H-functional layer that underlie the buffer layer.

Then, the EML may be formed on the HTL, H-functional layer, or buffer layer by vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed by using the compound according to an embodiment or various suitable hosts and dopants. The dopant may include both suitable fluorescent and phosphorescent dopants.

For example, as the suitable host, $Alq_3$, 4,4'-N,N'-dicarbazole-biphenyl (CBP), poly(n-vinyl carbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyryl arylene (DSA), dmCBP (see Formula below), and Compounds 501 to 509 below may be used, but the host is not limited thereto.

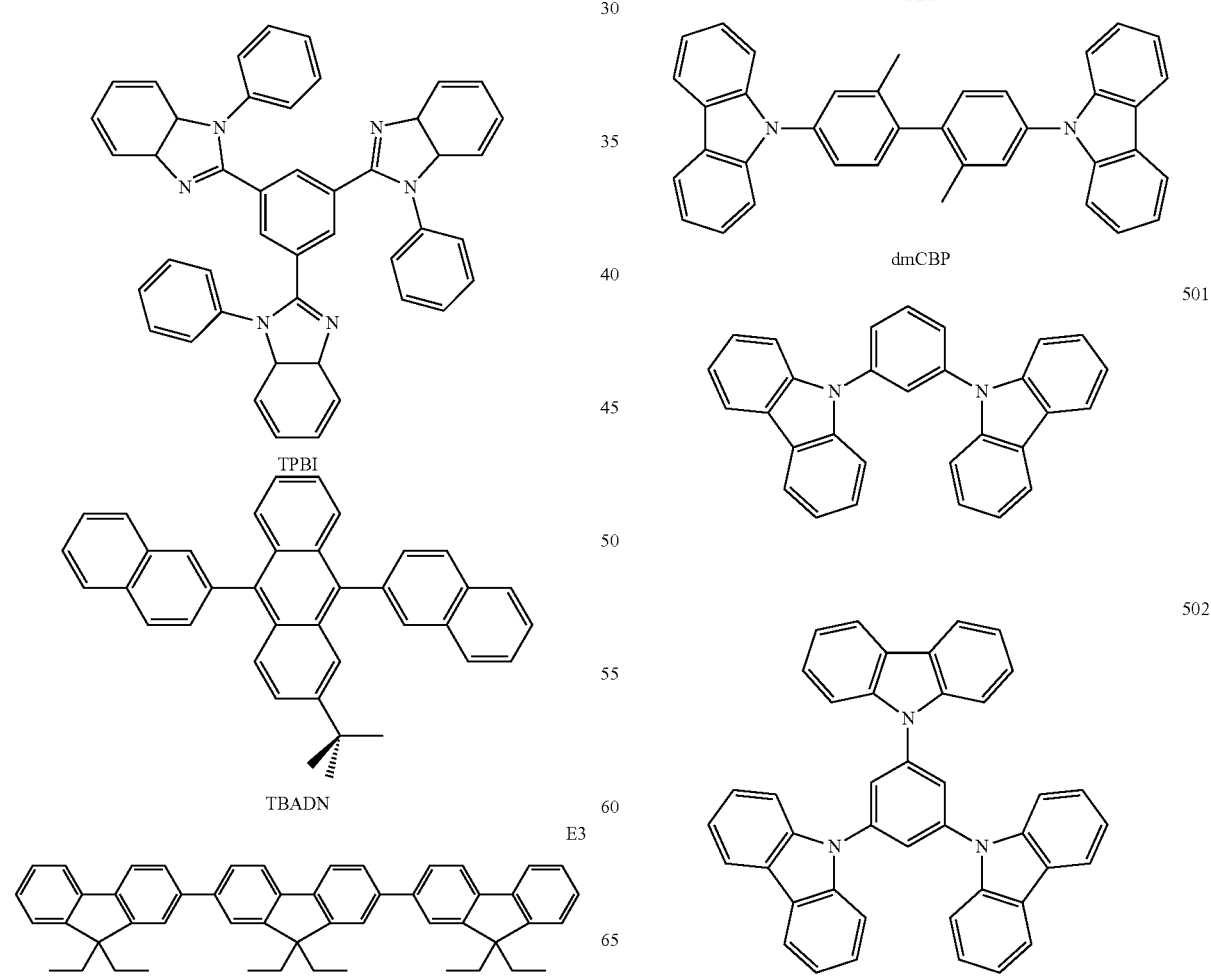

503
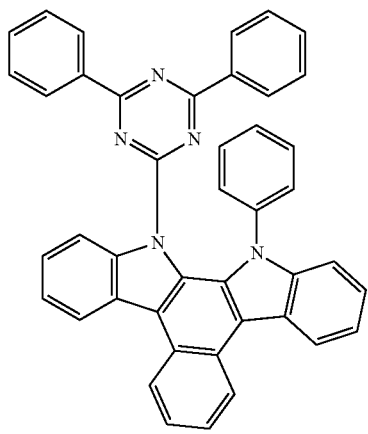
504
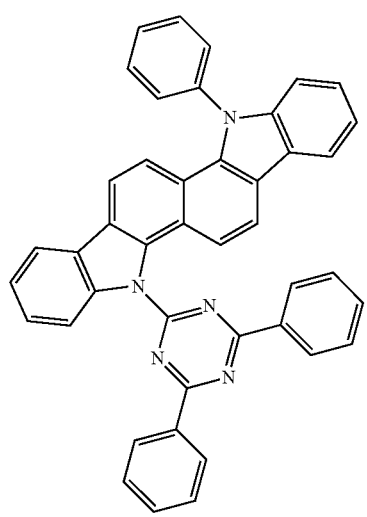
505
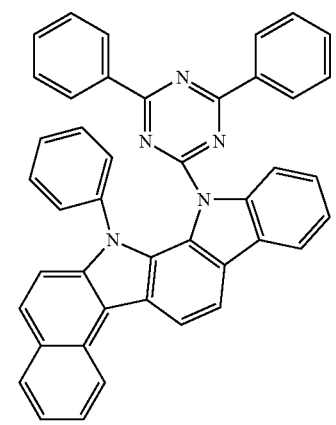
506
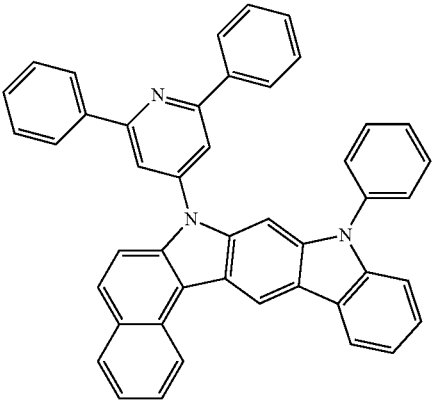
507
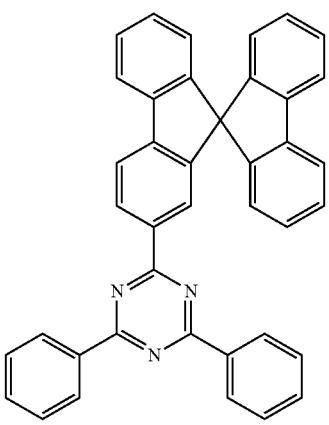
508
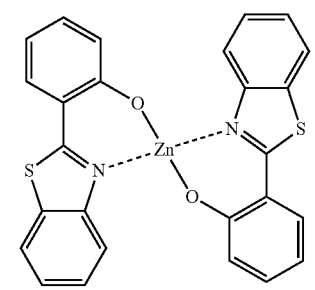
509
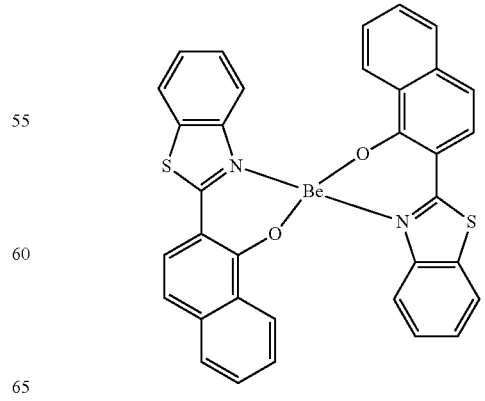

In an implementation, as the host, an anthracene-based compound represented by Formula 400 below may be used:

<Formula 400>

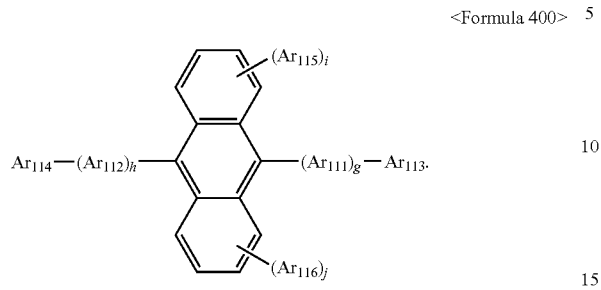

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently a substituted or unsubstituted $C_1$-$C_{10}$ alkyl group or a substituted or unsubstituted $C_5$-$C_{60}$ aryl group; and g, h, i, and j are each independently an integer of 0 to 4.

For example, in Formula 400 above, $Ar_{111}$ and $Ar_{112}$ may be a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, and an anthryl group, but they are not limited thereto.

In Formula 400 above, g, h, i, and j may be each independently, 0, 1, or 2.

In Formula 400 above, $Ar_{113}$ to $Ar_{116}$ may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group, each substituted with at least one of a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

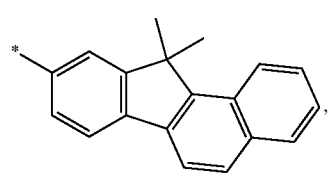 [SMILES: *c1ccc2c(c1)C(C)(C)c1c-2ccc2ccccc12]

but they are not limited thereto.

For example, an anthracene-based compound represented by Formula 400 above may be any one of compounds below, but it is not limited thereto:

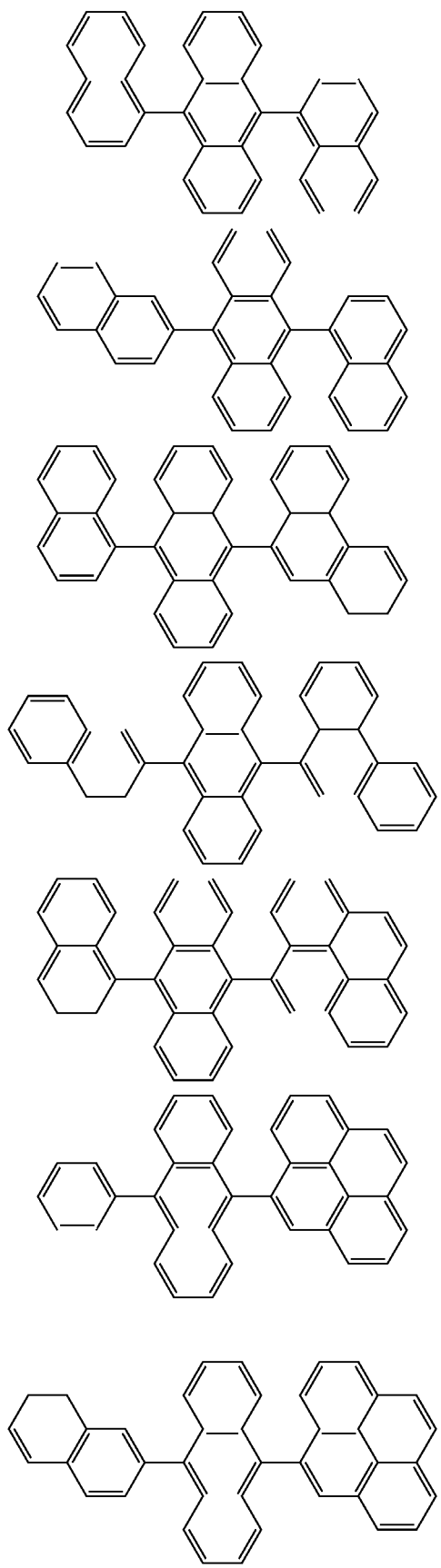

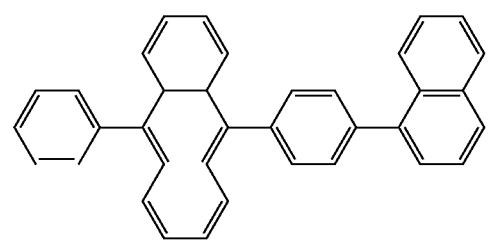
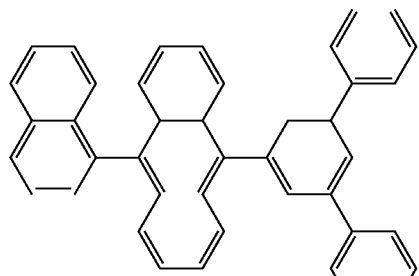
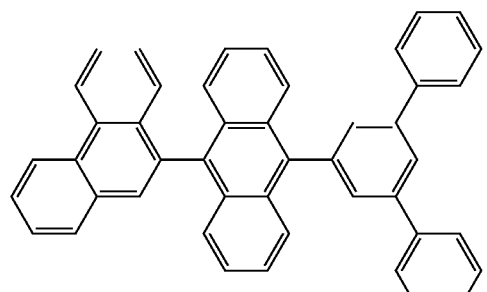
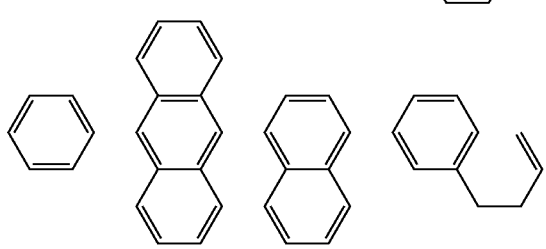
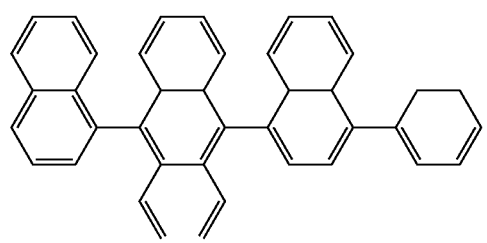
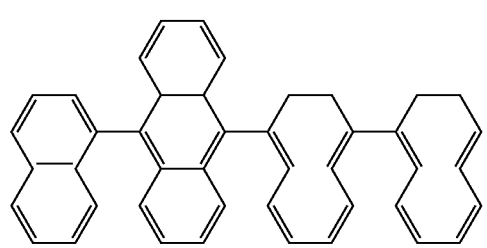
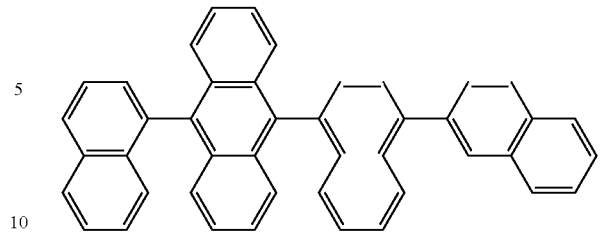
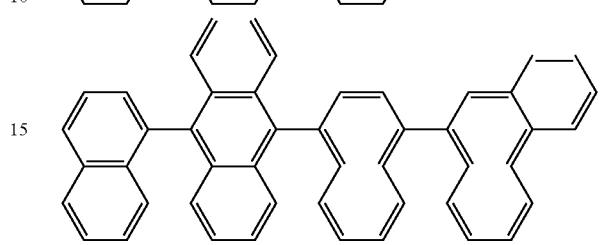
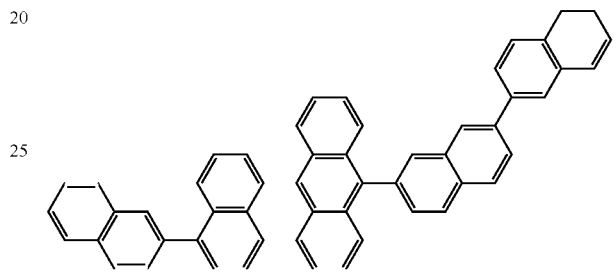
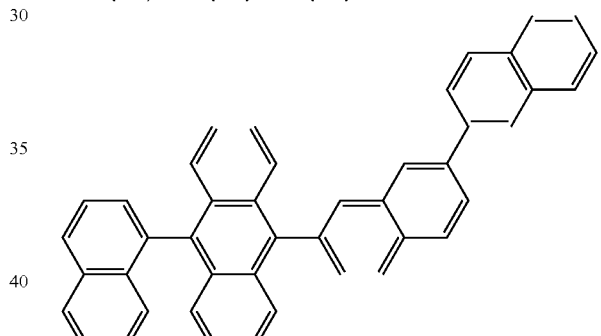
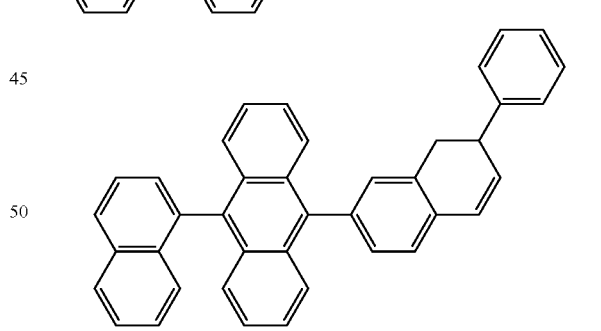
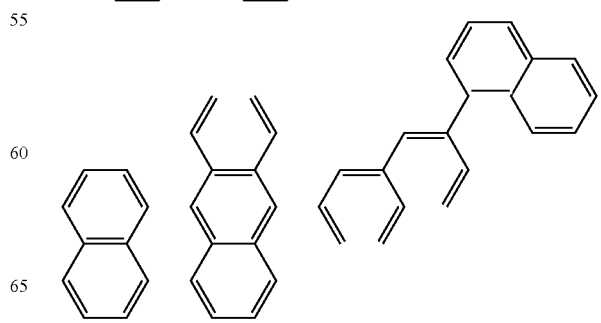

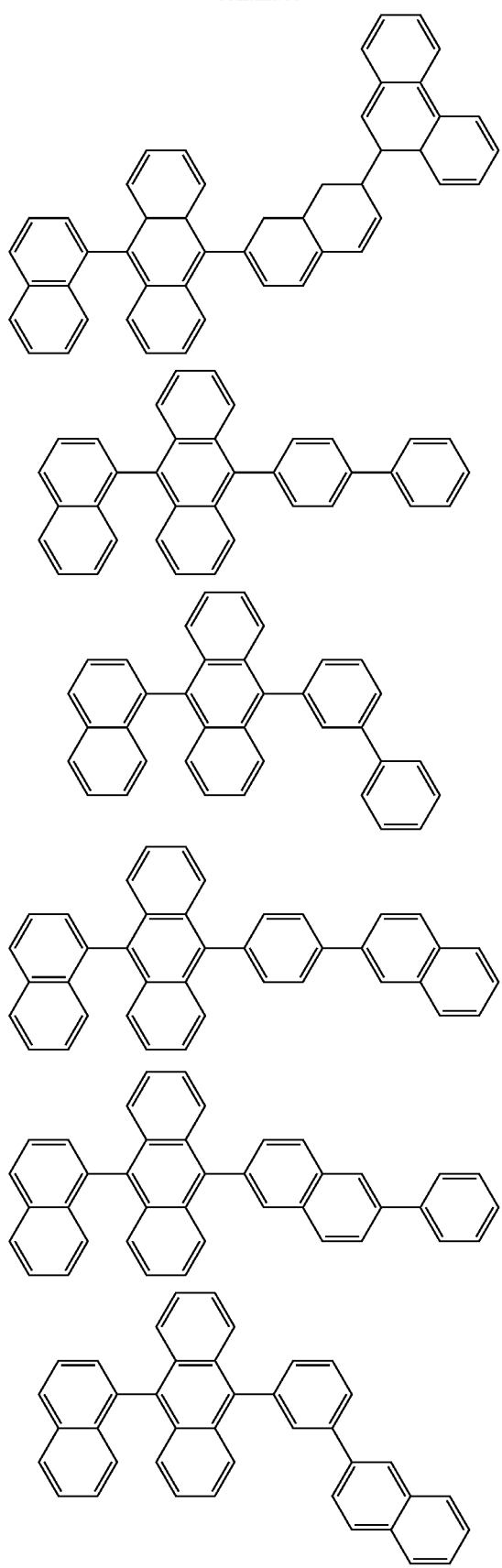
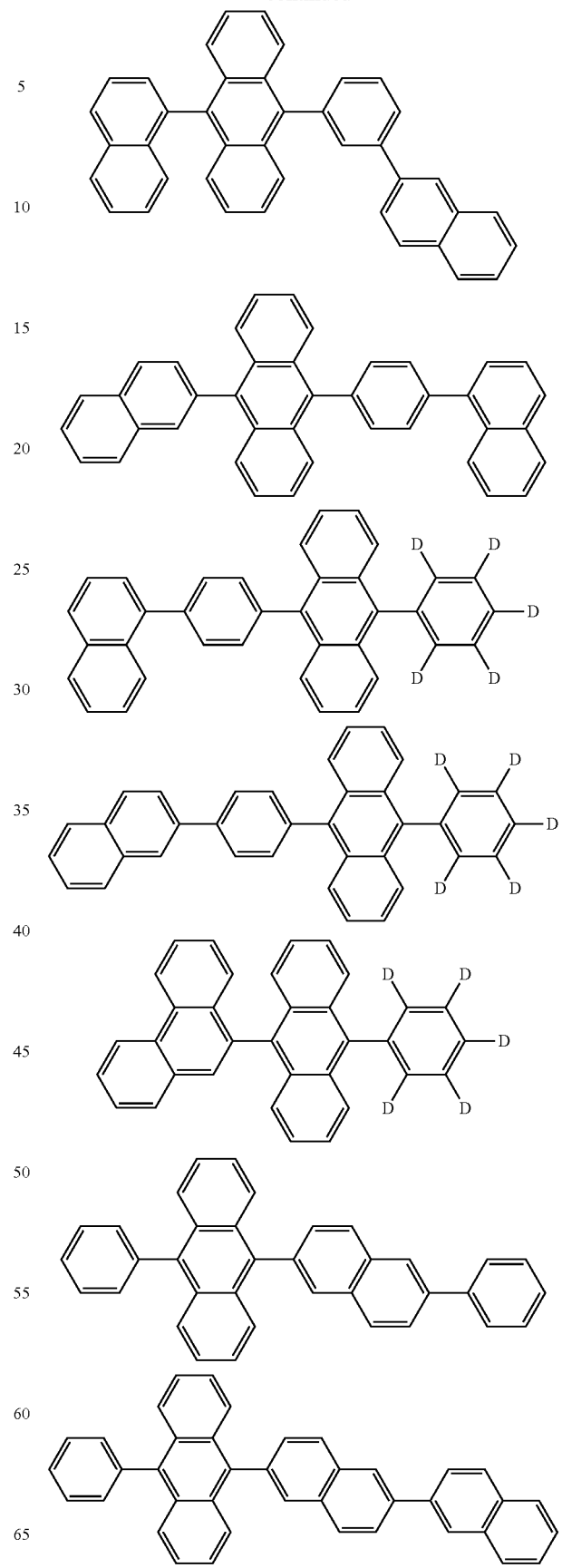

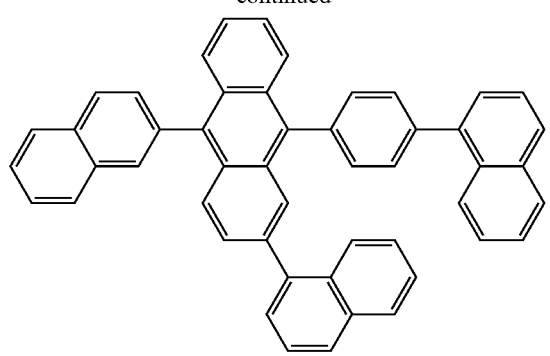
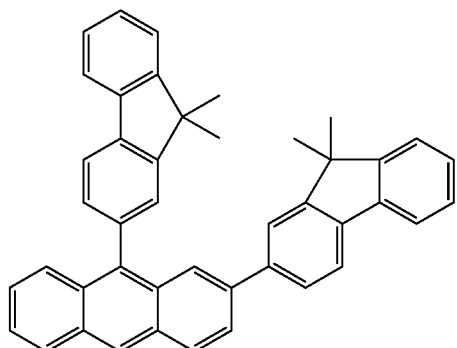
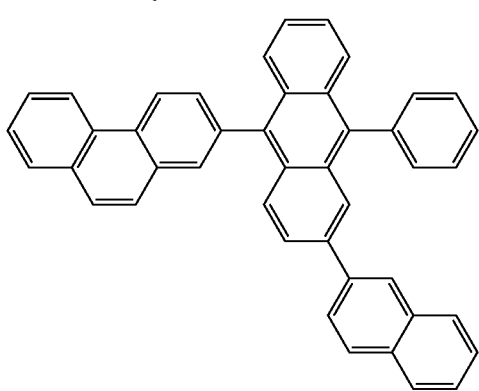

In an implementation, as the host, an anthracene-based compound represented by Formula 401 may be used:

<Formula 401>

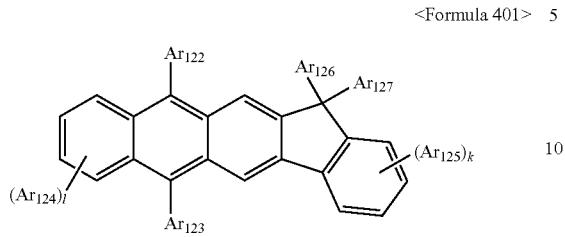

In Formula 401 above, detailed descriptions of $Ar_{122}$ to $Ar_{125}$ are as described in the description of $Ar_{113}$ of Formula 400 above.

In Formula 401 above, $Ar_{126}$ and $Ar_{127}$ are each independently a $C_1$-$C_{10}$ alkyl group (for example, a methyl group, an ethyl group, or a propyl group).

In Formula 401, k and l may be each independently an integer of 0 to 4. For example, k and l may be each independently an integer of 0, 1, or 2.

For example, the anthracene-based compound represented by Formula 401 above may be one of the compounds below, but it is not limited thereto:

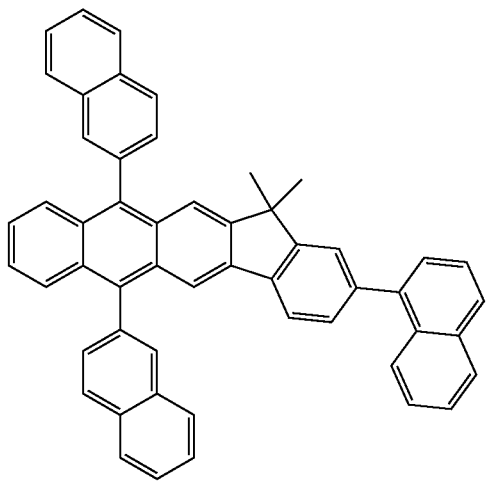

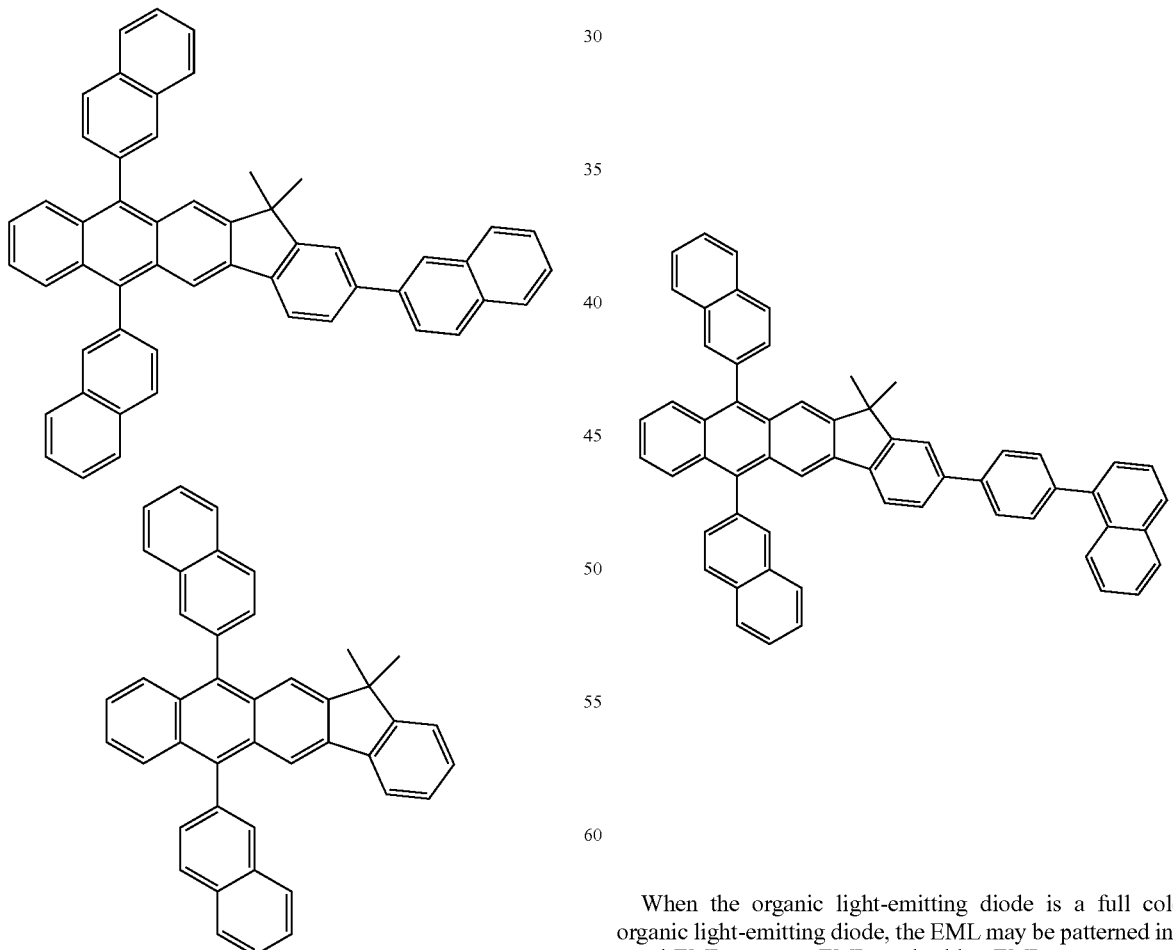

When the organic light-emitting diode is a full color organic light-emitting diode, the EML may be patterned into a red EML, a green EML, and a blue EML.

At least one of the red EML, the green EML, and the blue EML may include a dopant below (ppy=phenylpyridine).

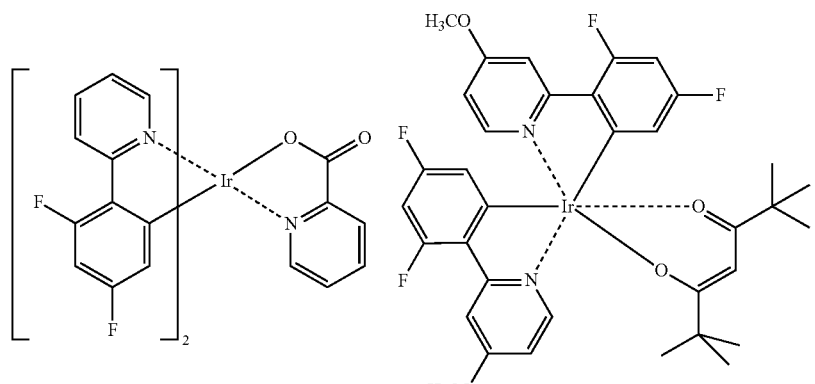
F₂Irpic                (F₂ppy)₂Ir(tmd)
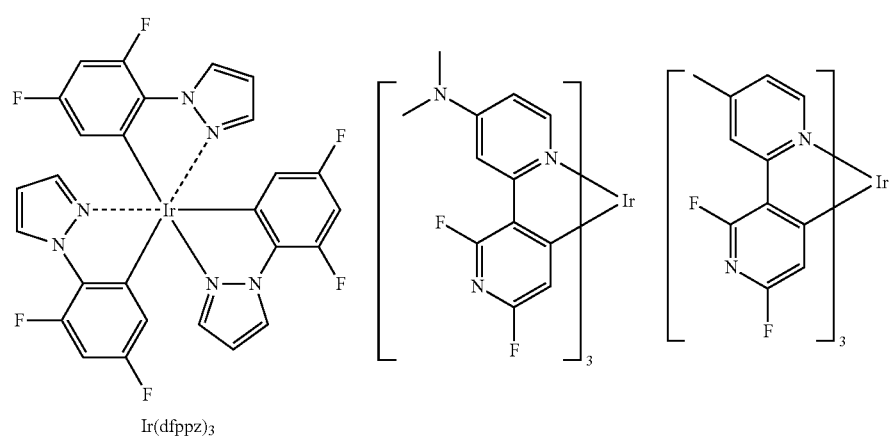
Ir(dfppz)₃
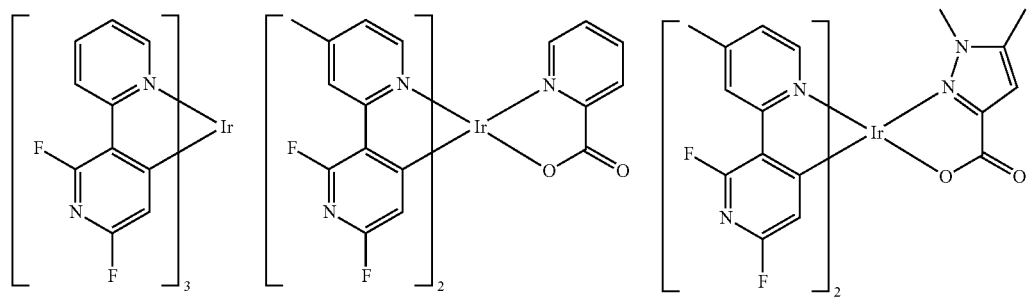
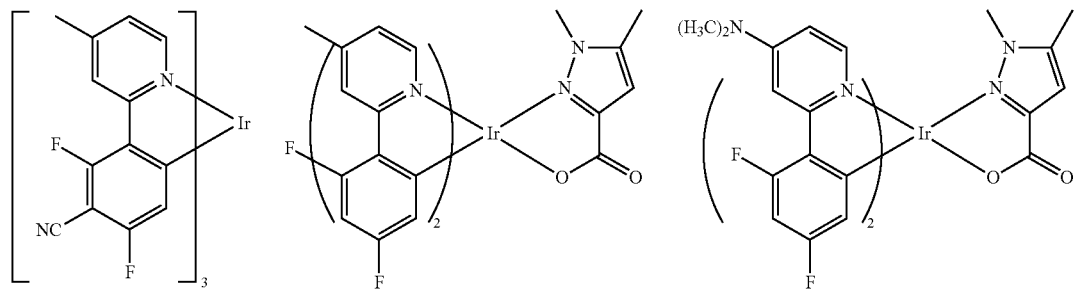

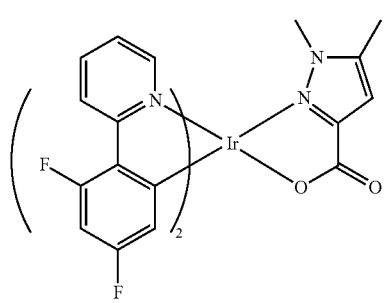
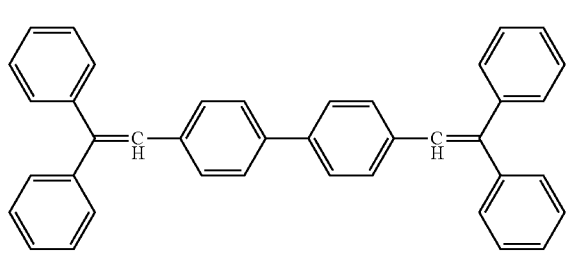
DPVBi
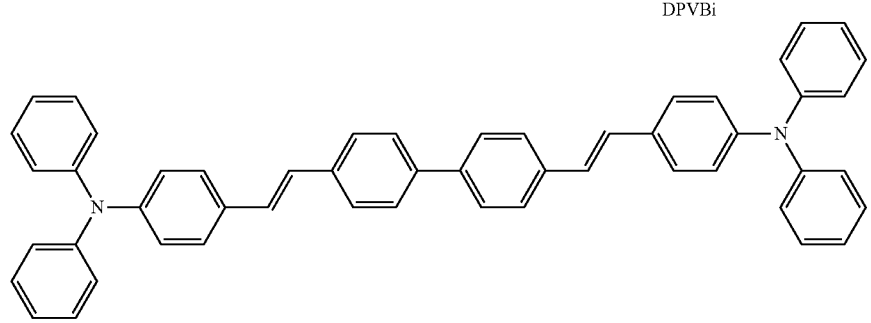
DPAVBi
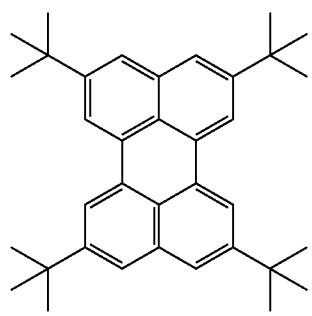
TBPe
For example, the compounds below may be used as the red dopant, but they are not limited thereto.
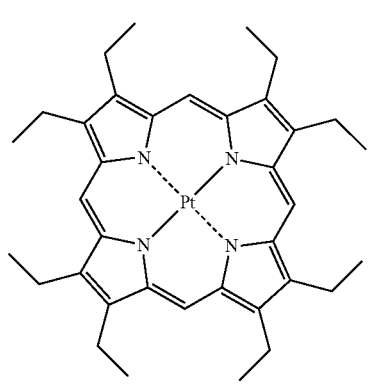
PtOEP
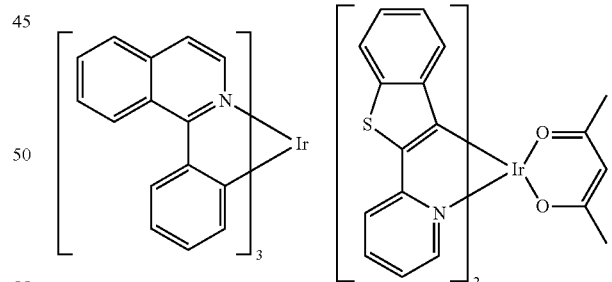
Ir(piq)$_3$    Btp$_2$Ir(acac)
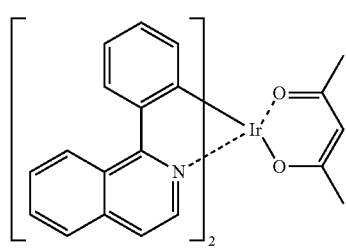

-continued
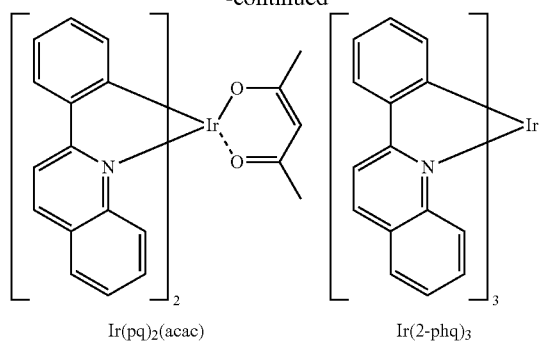
Ir(pq)₂(acac)  Ir(2-phq)₃
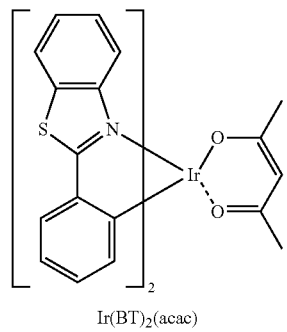
Ir(BT)₂(acac)
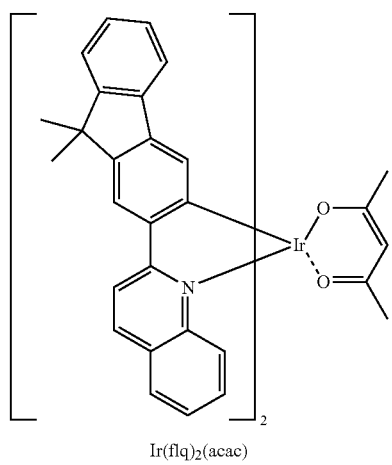
Ir(flq)₂(acac)
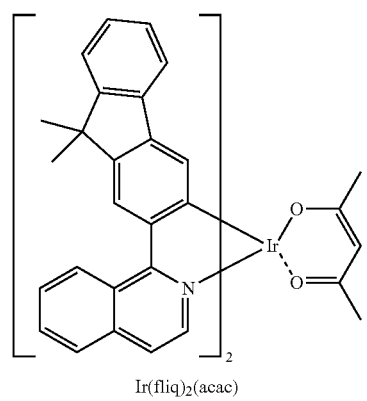
Ir(fliq)₂(acac)
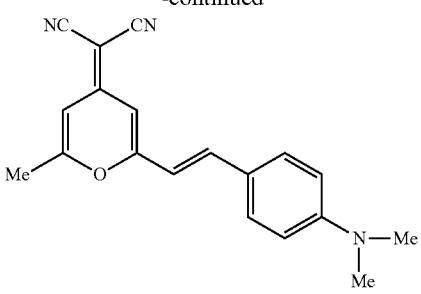
DCM
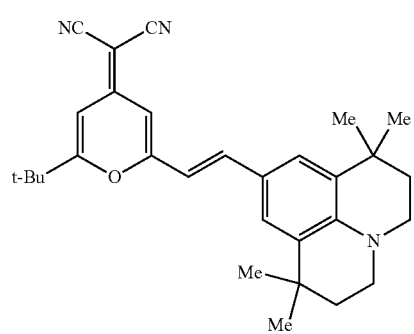
DCJTB
For example, the compounds below may be used as the green dopant, but the compounds are not limited thereto.
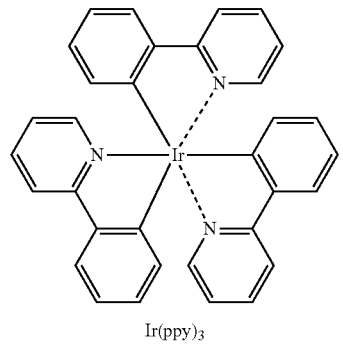
Ir(ppy)₃
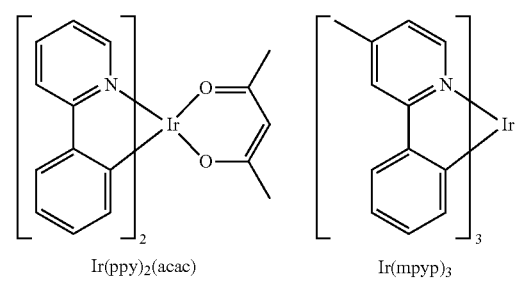
Ir(ppy)₂(acac)  Ir(mpyp)₃

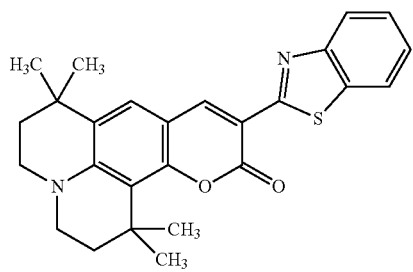
C545T
The dopant that may be included in the EML may be a Pd-complex or a Pt-complex as described or shown below, but the dopant is not limited thereto:
D1
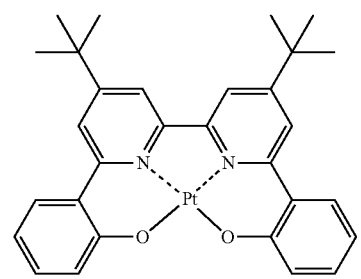
D2
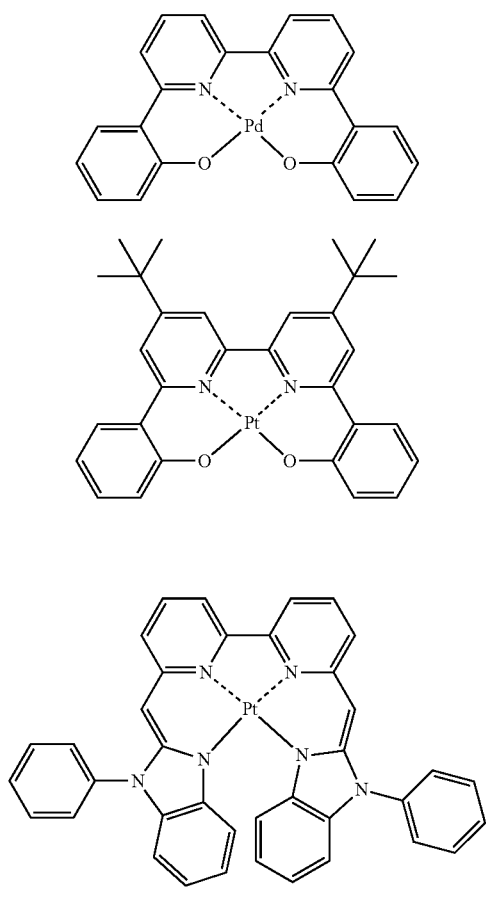
D3
D4
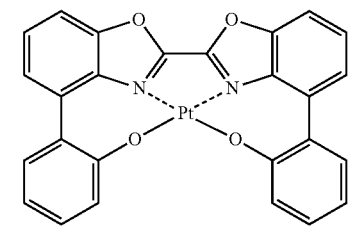
D5
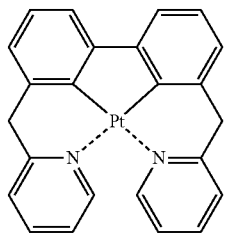
D6
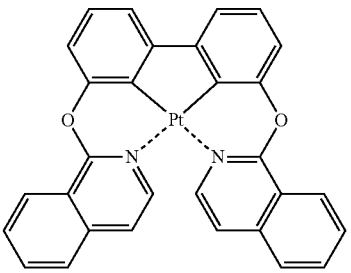
D7
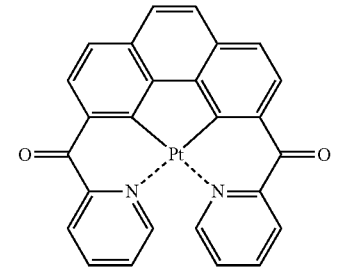
D8
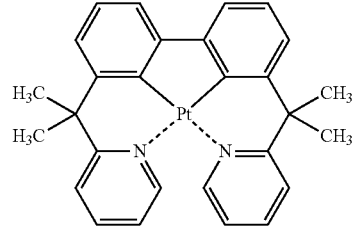
D9
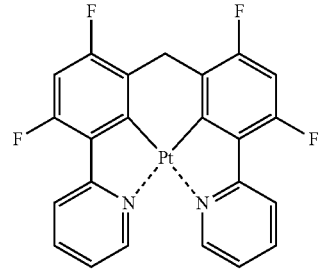
D10
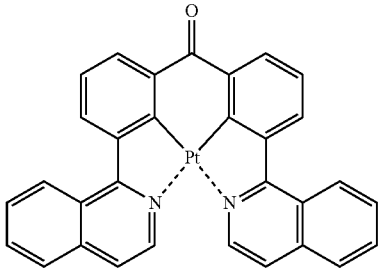

-continued
D11
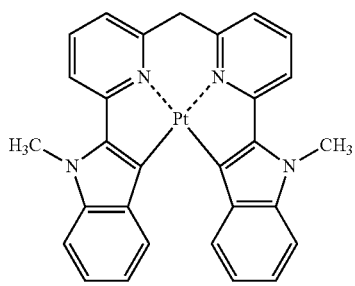
D12
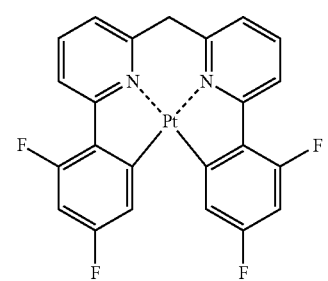
D13
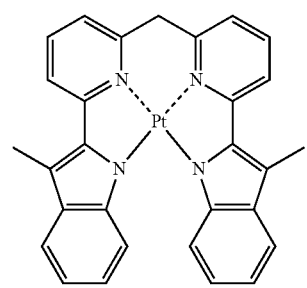
D14
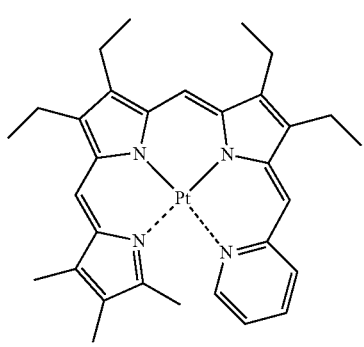
D15
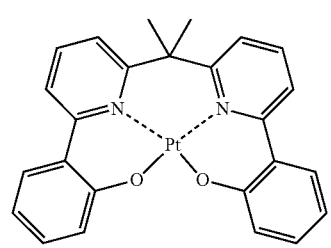
-continued
D16
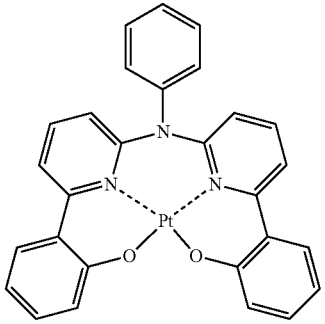
D17
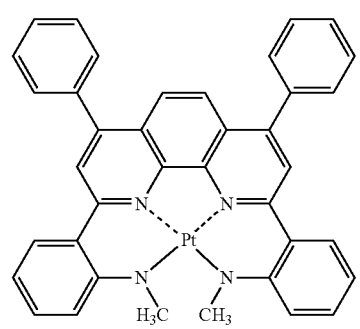
D18
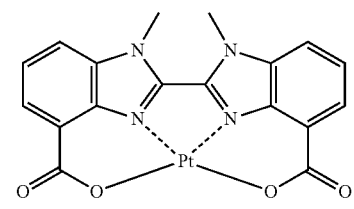
D19
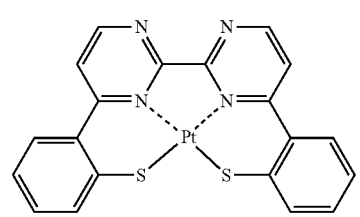
D20

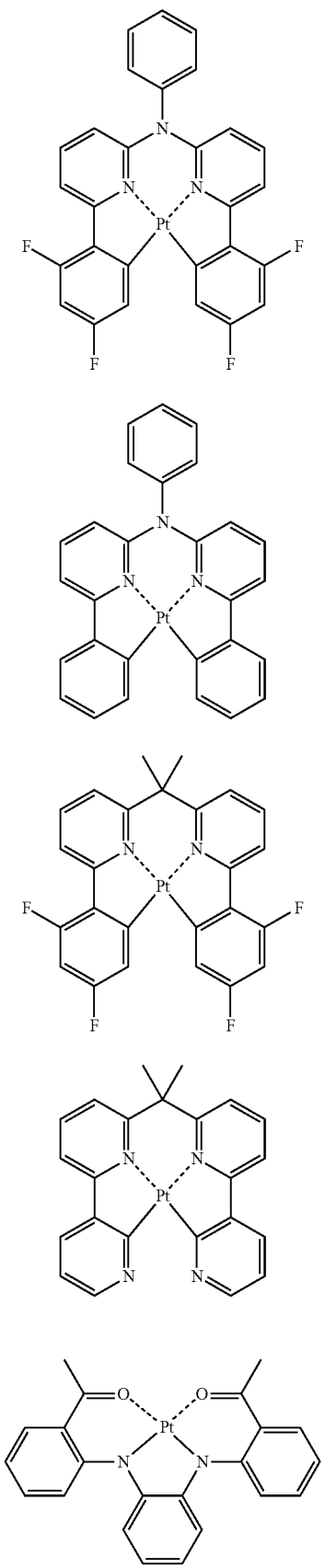
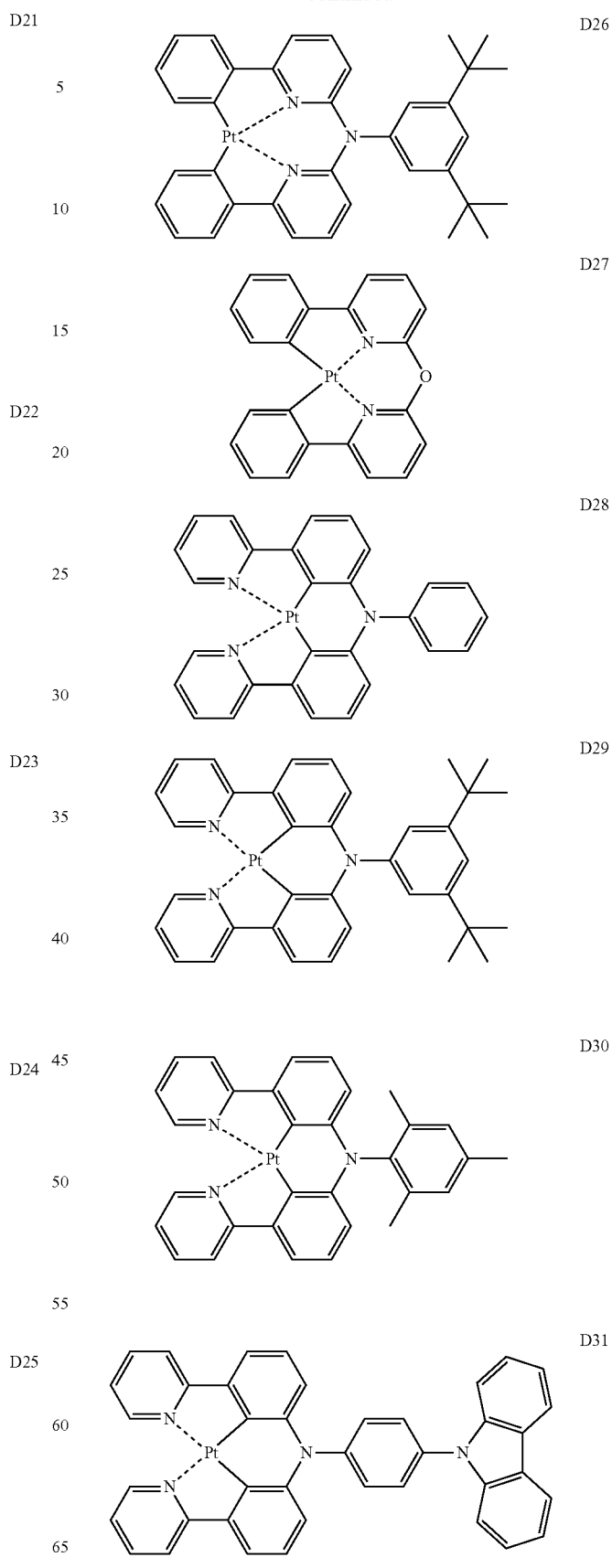

D32 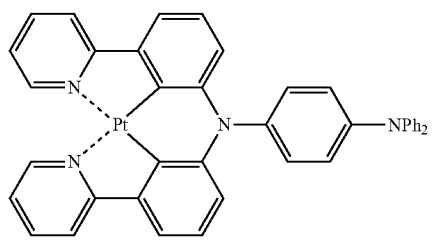
D33 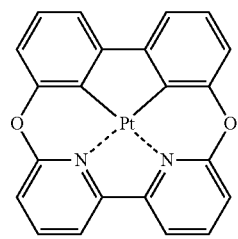
D34 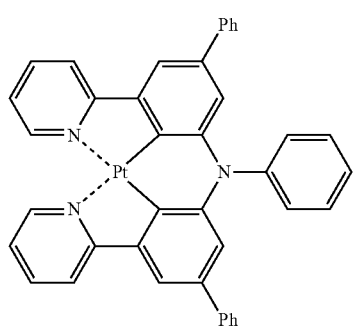
D35 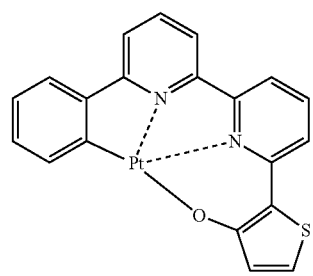
D36 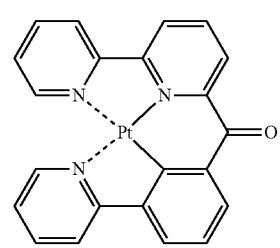
D37 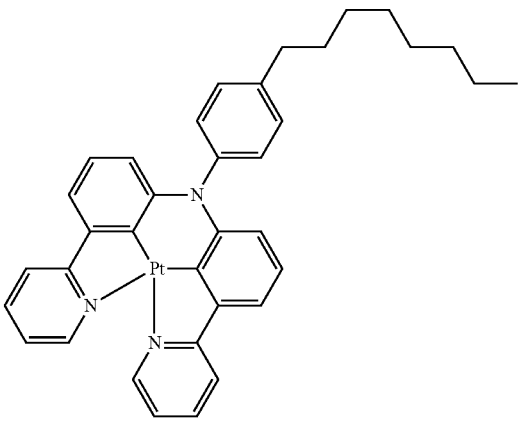
D38 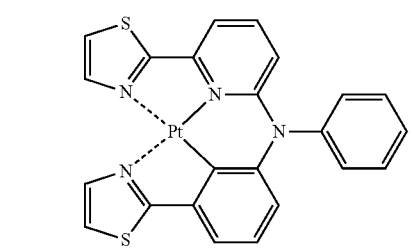
D39 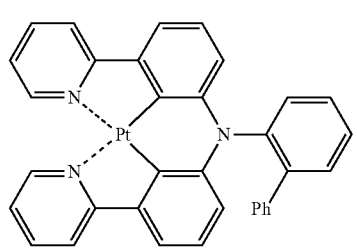
D40 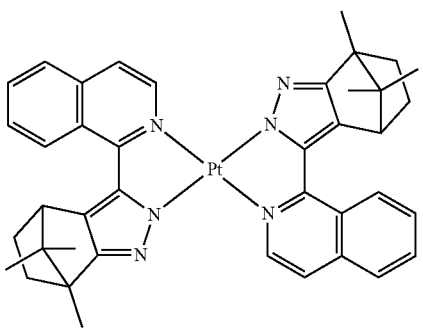
D41 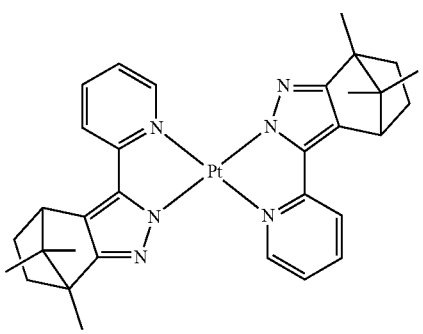

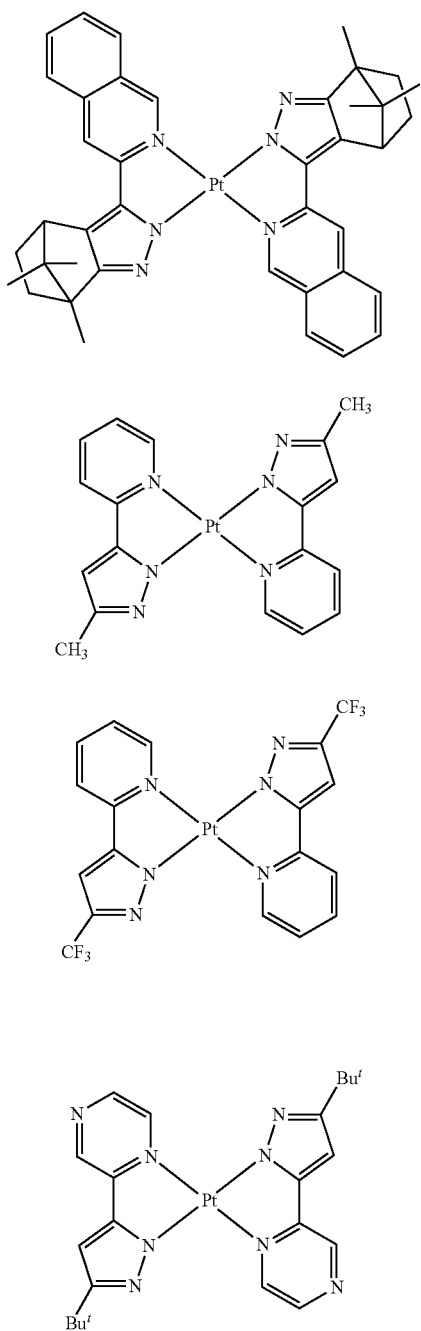
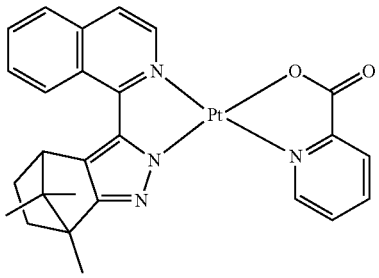
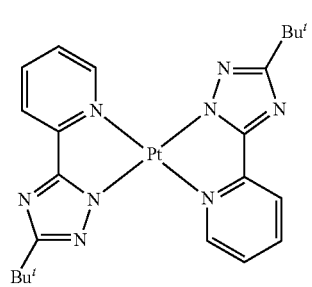
In an implementation, the dopant that may be included in the EML may be an Os-complex as described or shown below, but the dopant is not limited thereto:

-continued

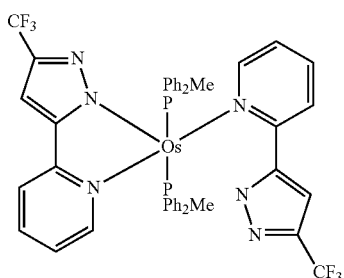
Os(fppz)₂(PPh₂Me)₂

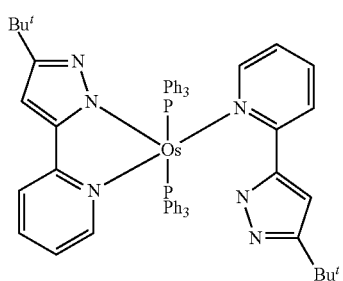
Os(bppz)₂(PPh₃)₂

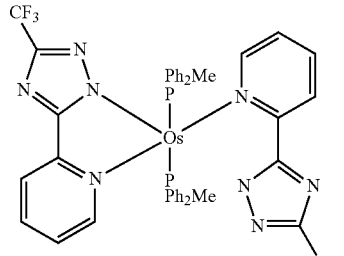
Os(fptz)₂(PPh₂Me)₂

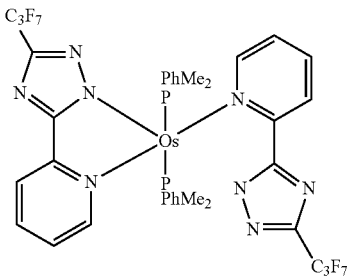
Os(hptz)₂(PPhMe₂)₂

When the EML includes a host and a dopant, an amount of the dopant in the EML may be about 0.01 parts by weight to about 15 parts by weight, based on 100 parts by weight of the host, but the amount is not limited thereto.

A thickness of the EML may be about 100 Å to about 1,000 Å, e.g., about 200 Å to about 600 Å. When the thickness of the EML is within these ranges, the EML may have good light-emitting ability without a substantial increase in driving voltage.

Then, the ETL may be formed on the EML by any of a variety of methods, for example, vacuum deposition, spin coating, or casting. When the ETL is formed using vacuum deposition or spin coating, the deposition and coating conditions may be similar to those for the formation of the HIL, though the deposition and coating conditions may vary according to a compound that is used to form the ETL.

The material of the ETL may include the compound according to an embodiment or a suitable material that can stably transport electrons injected from an electron-injecting electrode (cathode).

Non-limiting examples of materials for forming the ETL may include quinoline derivatives, such as tris(8-quinolinorate)aluminum (Alq3), TAZ, BAlq, beryllium bis(benzoquinolin-10-olate (Bebq2), 9,10-di(naphthalene-2-yl)anthracene (ADN), Compound 201, and Compound 202, but they are not limited thereto.

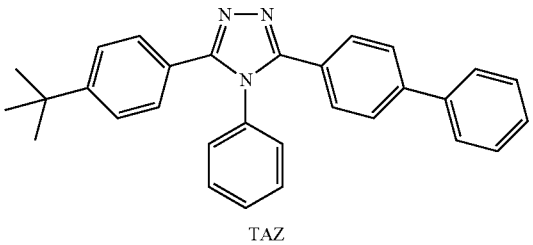
TAZ

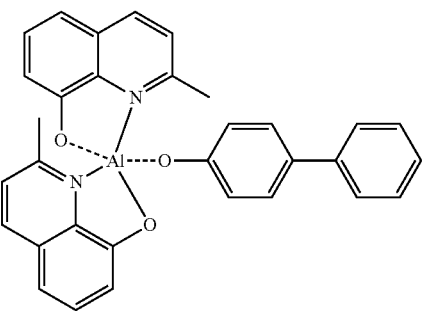
BAlq

<Compound 201>
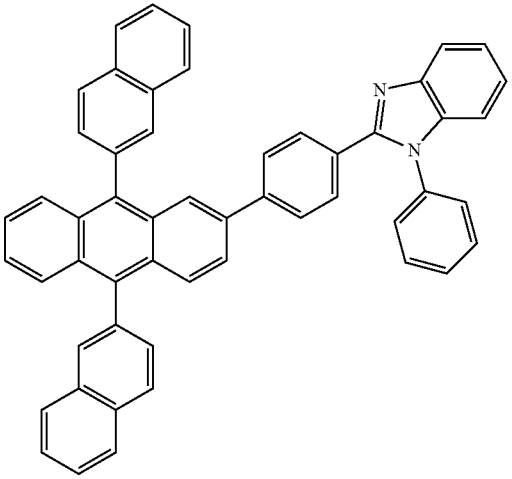

-continued

<Compound 202>

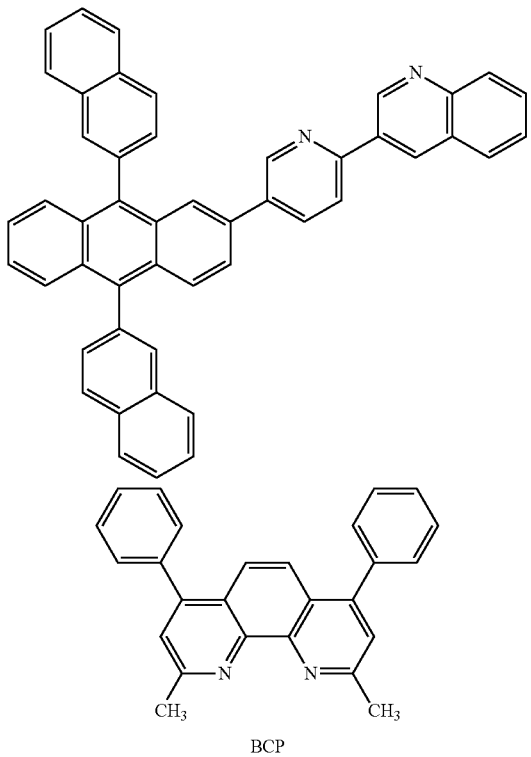

BCP

A thickness of the ETL may be from about 100 Å to about 1,000 Å, e.g., about 150 Å to about 500 Å. When the thickness of the ETL is within these ranges, the ETL may have satisfactory electron transporting ability without a substantial increase in driving voltage.

In an implementation, the ETL may further include a metal-containing material, in addition to a suitable electron-transporting organic compound.

The metal-containing material may include a Li complex. Non-limiting examples of the Li complex may include lithium quinolate (LiQ) and Compound 203 below:

<Compound 203>

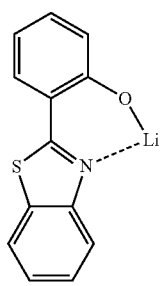

Then, the EIL, which facilitates injection of electrons from the cathode, may be formed on the ETL. A suitable electron-injecting material may be used to form the EIL.

Non-limiting examples of the materials for forming the EIL may include an EIL material such as LiF, NaCl, CsF, Li$_2$O, and BaO. The deposition and coating conditions for forming the EIL may be similar to those for the formation of the HIL, though the deposition and coating conditions may vary according to the compound that is used to form the EIL.

A thickness of the EIL may be about 1 Å to about 100 Å, e.g., about 3 Å to about 90 Å. When the thickness of the EIL is within these ranges, the EIL may have satisfactory electron injection ability without a substantial increase in driving voltage.

The second electrode may be disposed on the organic layer. The second electrode may be a cathode that is an electron injection electrode, wherein a material for forming the second electrode may be a metal, an alloy, an electro-conductive compound, which have a low work function, or a mixture thereof. In an implementation, the second electrode may be formed of lithium (Li), magnesium (Mg), aluminum (Al), aluminum lithium (Al—Li), calcium (Ca), magnesium-indium (Mg—In), magnesium-silver (Mg—Ag), or the like, and may be formed as a thin film type transmission electrode. In an implementation, to manufacture a top-emission light-emitting device, the transmission electrode may be formed of indium tin oxide (ITO) or indium zinc oxide (IZO).

Although the OLED has been described with reference to FIG. 1, the OLED is not limited thereto.

When a phosphorescent dopant is used in the EML, an HBL may be formed between the ETL and EML or the E-functional layer and EML by using vacuum deposition, spin coating, casting, LB deposition, or the like, in order to help prevent diffusion of triplet excitons or holes into an ETL. When the HBL is formed using vacuum deposition or spin coating, the conditions for deposition and coating may be similar to those for the formation of the HIL, although the conditions for deposition and coating may vary according to the material that is used to form the HBL. A suitable hole-blocking material may be used, and non-limiting examples of the suitable hole-blocking material may include oxadiazole derivatives, triazole derivatives, phenanthroline derivatives, and the like. In an implementation, BCP shown below may be used as a hole-blocking material.

BCP

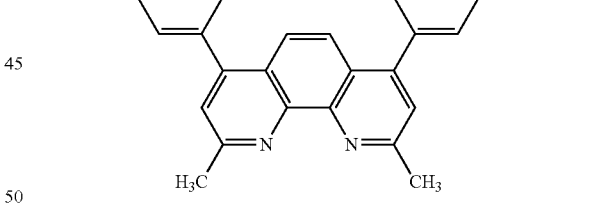

A thickness of the HBL may be about 20 Å to about 1,000 Å, e.g., about 30 Å to about 300 Å. When the thickness of the HBL is within these ranges, the HBL may have improved hole blocking ability without a substantial increase in driving voltage.

An organic light-emitting diode according to an embodiment may be included in various forms of flat display devices, e.g., passive matrix organic light-emitting display devices and active matrix organic light-emitting display devices. When the organic light-emitting device is included in an active matrix organic light-emitting display device, a first electrode (on a side of a substrate) may be electrically connected to a source electrode or a drain electrode of a thin film transistor as a pixel electrode. In an implementation, the organic light-emitting diode may be included in a flat display device capable of displaying on both sides thereof.

In an implementation, an organic layer of an organic light-emitting diode may be formed by a deposition method using a compound according to an embodiment or by a wet method that involves coating the compound prepared as a solution.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 1

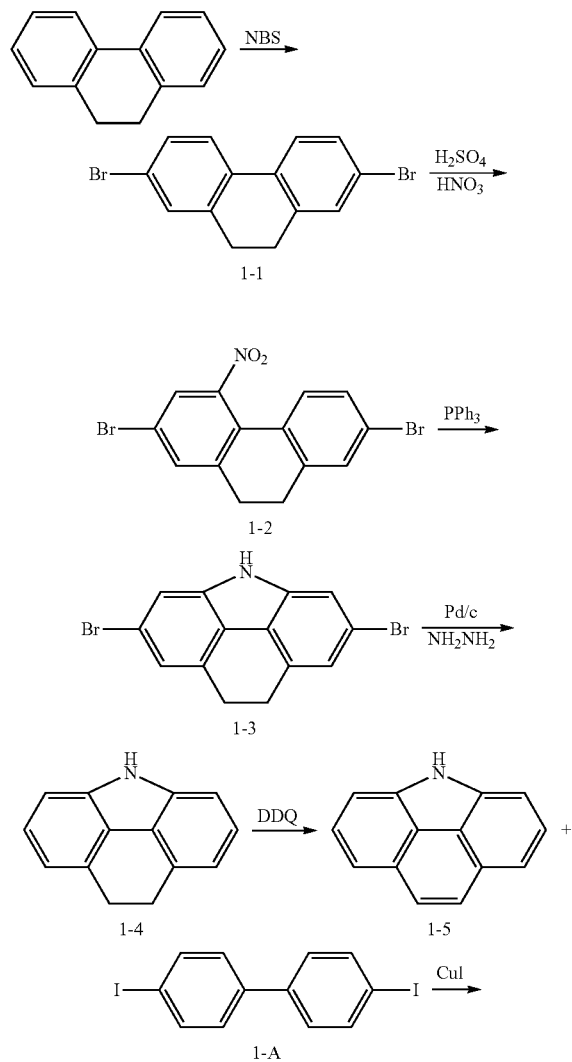

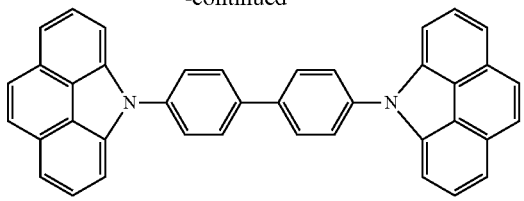

Synthesis of Intermediate 1-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile to prepare a reaction solution, and then the reaction solution was stirred at a temperature of 50° C. for 12 hours. After cooling the reaction solution to room (e.g., ambient) temperature, the reaction solution was stirred for 30 minutes and then crystals were precipitated therefrom. The crystals were collected by using a reduced pressure filter, and then the crystals were washed with methanol to obtain 8.4 g of gray crystals of Intermediate I-1 (yield 45%). The compounds produced were observed through liquid chromatography-mass spectrometry (LC-MS). $C_{14}H_{10}Br_2$ $M^+$ 336.9

Synthesis of Intermediate 1-2

5.0 g (15.0 mmol) of Intermediate 1-1 was completely dissolved in 50 mL of dichloromethane to prepare a mixture, then 1.7 g (30.0 mmol) of nitric acid was added to the mixture at room temperature, and then 1.5 g (15.0 mmol) of sulfuric acid was slowly drop-wise added to the mixture, followed by stirring the mixture at a temperature of 30° C. for 6 hours. After completing the above reaction, the mixture was cooled to room temperature, and then 50 mL of methanol was added to the mixture, followed by stirring the mixture for 2 hours to precipitate crystals. The crystals were collected by using a reduced pressure filter, and then the crystals were washed with methanol to obtain 5.2 g (yield 90%) of yellow crystals of Intermediate 1-2. The compounds produced were observed through LC-MS. $C_{14}H_9Br_2NO_2$ $M^+$ 381.9

Synthesis of Intermediate 1-3

4.6 g (12.0 mmol) of Intermediate 1-2 was dissolved and heated in 30 mL of o-dichlorobenzene to completely dissolve Intermediate 1-2 to prepare a reaction solution, and then 4.7 g (18.0 mmol) of triphenylphosphine was added to the reaction solution, followed by stirring the reaction solution at a temperature of 180° C. for 3 hours. After cooling the reaction solution to room temperature, a solvent was evaporated from the reaction solution to obtain residues, and then the residues were isolated and purified by using silica gel column chromatography to prepare an isolate, followed by washing the isolate with methanol to obtain 2.9 g (yield 70%) of white crystals of Intermediate 1-3. The compounds produced were observed through LC-MS. $C_{14}H_9Br_2N$ $M^+$ 349.9

Synthesis of Intermediate 1-4

After dissolving 10 g (28.5 mmol) of Intermediate 1-3 and 0.03 g (0.28 mmol) of Pd/c (10%) in 100 ml ethanol at room temperature to prepare a reaction solution, temperature of the reaction solution was increased to 50° C., and then 5.48 g (171 mmol) of hydrazine was drop-wise added to the reaction solution, followed by stirring the reaction solution for 24 hours. After cooling the reaction solution to room temperature, the reaction solution was washed with acetone, and 100 ml of ice water was added to the reaction solution to obtain 3.63 g (yield 66%) of white crystals of Intermediate 1-4. The compounds produced were observed through LC-MS. $C_{14}H_{11}N$ M+ 194.1

Synthesis of Intermediate 1-5

After dissolving 4.89 g (25.3 mmol) of Intermediate 1-4 in 100 ml of toluene in the presence of oxygen to prepare a reaction solution, 1.57 g (7.6 mmol) of 2,3-dichloro-5,6-dicyano-1,4-benzoquinone and 0.52 g (7.6 mmol) of $NaNO_2$ were added to the reaction solution at room temperature. After stirring the reaction solution at a temperature of 110° C. for 6 hours, and after the completion of the reaction described above, the reaction solution was cooled to room temperature, and then a solvent was evaporated from the reaction solution to obtain residues. The obtained residues were isolated and purified by using silica gel column chromatography to obtain 4.35 g (yield 90%) of Intermediate 1-5. The produced compounds were observed through LC-MS. $C_{20}H_{12}IN$ M+ 192.3

Synthesis of Compound 1

1.91 g (10.0 mmol) of Intermediate I-5, 8.53 g (21.0 mmol) of Compound 1-A, 0.4 g (2.0 mmol) of 1,10-phenanthroline, 0.4 g (4.0 mmol) of CuI, and 8.2 g (60.0 mmol) of $K_2CO_3$ were dissolved in 60 mL of N,N-dimethylformamide (DMF) to prepare a reaction solution, followed by stirring the reaction solution at a temperature of 80° C. for 24 hours. After cooling the reaction solution to room temperature, the reaction solution was extracted three times with 30 mL of water and 40 mL of diethyl ether to collect organic layers. The collected organic layers were dried with magnesium sulfate and then a solvent was evaporated therefrom to obtain residues. The obtained residues were isolated and purified by using silica gel column chromatography to obtain 5.32 g (yield 75%) of Compound 1. The synthesized compounds were observed through mass spectrometry/fast atom bombardment (MS/FAB) and $^1H$ NMR.

Synthesis Example 2

Synthesis of Compound 8

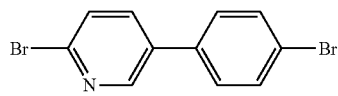

Compound 8 was synthesized in the same manner as in the synthesis of Compound 1 in Synthesis Example 1, except that Compound 8-A was used instead of Compound 1-A. The synthesized compounds were observed through MS/FAB and $^1H$ NMR.

Synthesis Example 3

Synthesis of Compound 18

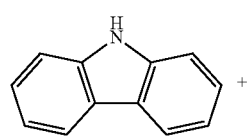

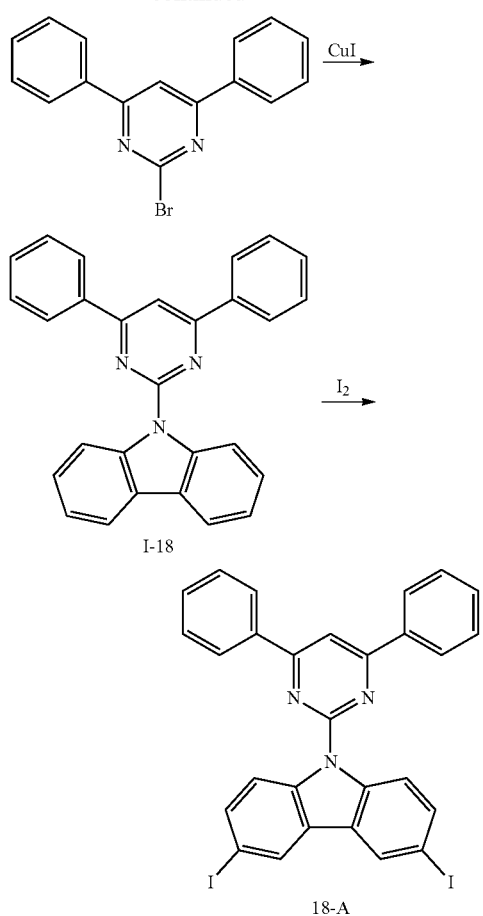

Synthesis of Intermediate I-18

Intermediate I-18 was synthesized in the same manner as in the synthesis of Compound 1 in Synthesis Example 1, except that 9H-carbazole was used instead of Intermediate 1-5,2-bromo-4,6-diphenyl pyrimidine was used instead of Compound 1-A. The synthesized compounds were observed through LC-MS. $C_{28}H_{19}N_3$ M+ 398.2

Synthesis of Intermediate 18-A 14.7 g (37.1 mmol) of Intermediate I-18 was completely dissolved in 100 ml of dichloromethane, and then 9.42 g (37.1 mmol) of iodine and 4.76 g (22.0 mmol) of $KIO_3$ were added by portions of 1/5 to prepare a reaction solution. After stirring the reaction solution for 6 hours, the reaction solution was washed with methanol to obtain 18.8 g (yield 78%) of Intermediate 18-A. The produced compounds were observed through LC-MS. $C_{28}H_{17}I_2N_3$ M+ 649.56

Synthesis of Compound 18

Compound 18 was synthesized in the same manner as in the synthesis of Compound 1 in Synthesis Example 1, except that Intermediate 18-A was used instead of Compound 1-A. The synthesized compounds were observed through MS/FAB and $^1H$ NMR.

Synthesis Example 4

Synthesis of Compound 28

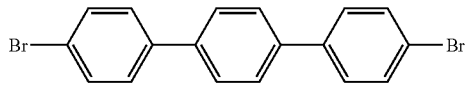

28-A

Compound 28 was synthesized in the same manner as in the synthesis of Compound 1 in Synthesis Example 1, except that Compound 28-A was used instead of Compound 1-A. The synthesized compounds were observed through MS/FAB and $^1$H NMR.

Synthesis Example 5

Synthesis of Compound 39

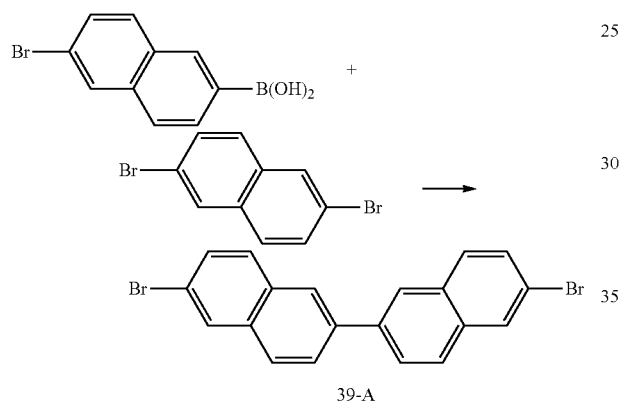

39-A

Synthesis of Intermediate 39-A 1.46 g (5.09 mmol) of 2,6-dibromonaphthalene, 0.75 g (2.99 mmol) of (6-bromonaphthalene-2-yl) boronic acid, 0.29 g (0.25 mmol) of tetrakis(triphenylphosphine)palladium (Pd(PPh$_3$)$_4$), and 0.62 g (4.48 mmol) of K$_2$CO$_3$ were dissolved in 60 ml of a mixed solution of THF/H$_2$O (a volume ratio of 2/1) to prepare a reaction solution, followed by stirring the reaction solution at a temperature of 70° C. for 5 hours. After cooling the reaction solution to room temperature, 40 ml of water was added to the reaction solution and extracted the reaction solution three times with 50 ml of diethyl ether to collect organic layers. The collected organic layers were dried with magnesium sulfate and a solvent was evaporated therefrom to obtain residues. The obtained residues were isolated and purified by using silica gel column chromatography to obtain 0.91 g of Intermediate 39-A (yield 74%). The produced compounds were observed through LC-MS. C$_{20}$H$_{12}$Br$_2$ M+ 410.56

Synthesis of Compound 39

Compound 39 was synthesized in the same manner as in the synthesis of Compound 1 in Synthesis Example 1, except that Intermediate 39-A was used instead of Compound 1-A. The synthesized compounds were observed through MS/FAB and $^1$H NMR.

Synthesis Example 6

Synthesis of Compound 46

46-A

Synthesis of Intermediate 46-A

Intermediate 46-A was synthesized in the same manner as in the synthesis of Intermediate 39-A in Synthesis Example 5, except that 4-bromo-iodobenzene was used instead of 2,6-dibromonaphthalene, and that (10-bromoanthracene-9-yl)boronic acid was used instead of (6-bromonaphthalene-2-yl)boronic acid. The synthesized compounds were observed through MS/FAB and $^1$H NMR. The synthesized compounds were observed through LC-MS. C$_{20}$H$_{12}$Br$_2$ M+ 410.54

Synthesis of Compound 46

Compound 46 was synthesized in the same manner as in the synthesis of Compound 1 in Synthesis Example 1, except that Intermediate 46-A was used instead of Compound 1-A. The synthesized compounds were observed through MS/FAB and $^1$H NMR.

Synthesis Example 7

Synthesis of Compound 56

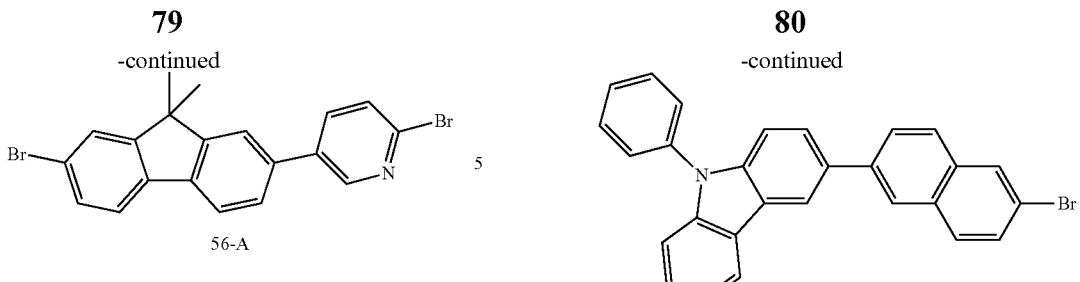

56-A

Synthesis of Intermediate 56-A

Intermediate 56-A was synthesized in the same manner as in the synthesis of Intermediate 39-A in Synthesis Example 5, except that 2-bromo-5-iodopyridine was used instead of 2,6-dibromonaphthalene, and that (7-bromo-9,9-dimethyl-9H-fluorene-2-yl)boronic acid was used instead of (6-bromonaphthalene-2-yl)boronic acid. The synthesized compounds were observed through LC-MS. $C_{20}H_{15}Br_2N$ M+ 427.99

Synthesis of Compound 56

Compound 56 was synthesized in the same manner as in the synthesis of Compound 1 in Synthesis Example 1, except that Intermediate 56-A was used instead of Compound 1-A. The synthesized compounds were observed through MS/FAB and $^1$H NMR.

Synthesis Example 8

Synthesis of Compound 63

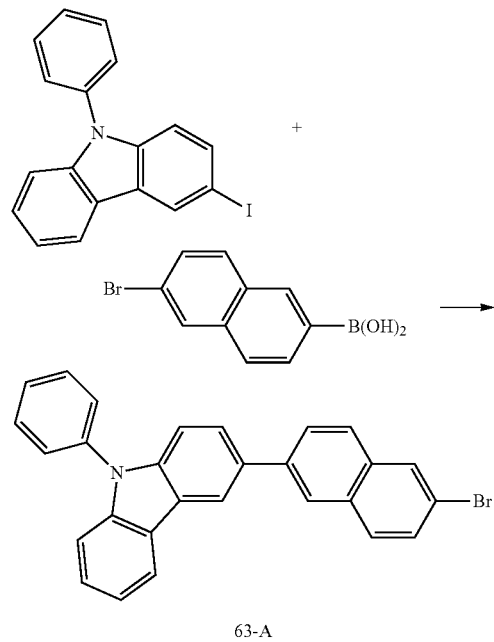

63-B

Synthesis of Intermediate 63-A

Intermediate 63-A was synthesized in the same manner as in the synthesis of Intermediate 39-A in Synthesis Example 5, except that 3-iodo-9-phenyl-9H-carbazole was used instead of 2,6-dibromonaphthalene. The synthesized compounds were observed through MS/FAB and $^1$H NMR. The synthesized compounds were observed through LC-MS. $C_{28}H_{18}BrN$ M+ 448.1

Synthesis of Intermediate 63-B 16 g (37.1 mmol) of Intermediate 63-A was completely dissolved in 100 ml of dichloromethane, and then 3.58 g (14.1 mmol) of iodine and 2.38 g (11.13 mmol) of $KIO_3$ were added in portions of 1/5 to prepare a reaction solution. After stirring the reaction solution for 6 hours, the reaction solution was washed with methanol to obtain 11.7 g (yield 55%) of Intermediate 63-B. The compounds produced were observed through LC-MS. $C_{28}H_{17}BrIN$ M+ 573.99

Synthesis of Compound 63

Compound 63 was synthesized in the same manner as in the synthesis of Compound 1 in Synthesis Example 1, except that Intermediate 63-A was used instead of Compound 1-A. The synthesized compounds were observed through MS/FAB and $^1$H NMR.

Additional compounds were synthesized by using the same synthesis methods as in the synthesis pathways described above, and using suitable intermediate materials. Table 1 below shows $^1$H NMR and MS/FAB results of the synthesized compounds described above.

Compounds other than the compounds listed in Table 1 below, may be considered in view of the synthesis pathways and source materials described above.

TABLE 1

| Compound | $^1$H NMR (CDCl$_3$, 400 MHz) | MS/FAB found | MS/FAB calculated |
|---|---|---|---|
| 1 | δ = 7.70-7.66 (m, 4H), 7.56-7.44 (m, 16H), 7.37-7.34 (m, 4H), | 532.33 | 532.19 |
| 4 | δ = 7.70-7.76 (m, 4H), 7.61-7.59 (dd, 4H), 7.55-7.52 (d, 4H), 7.51-7.45 (m, 6H), 7.36-7.33 (m, 2H), 7.04-7.01 (m, 2H) | 568.32 | 568.18 |
| 5 | δ = 7.70-7.76 (m, 4H), 7.55-7.52 (d, 4H), 7.51-7.44 (m, 8H) | 540.40 | 540.24 |

TABLE 1-continued

| Compound | $^1$H NMR (CDCl$_3$, 400 MHz) | MS/FAB found | MS/FAB calculated |
|---|---|---|---|
| 8 | δ = 8.53-8.51 (m, 1H), 8.09-8.06 (m, 1H), 7.77-7.72 (m, 6H), 7.51-7.44 (m, 12H), 7.40-7.35 (m, 3H) | 533.25 | 533.19 |
| 9 | δ = 7.70-7.76 (m, 4H), 7.59-7.45 (m, 14H), 7.31-7.29 (d, 2H), 7.13-7.10 (dd, 2H), 1.60 (s, 6H) | 572.35 | 572.23 |
| 12 | δ = 7.80-7.74 (m, 6H), 7.54-7.48 (m, 12H), 7.35-7.32 (m, 2H), 7.23-7.21 (m, 2H), 0.27 (s, 6H) | 588.29 | 588.20 |
| 13 | δ = 7.86-7.84 (m, 2H), 7.78-7.72 (m, 4H), 7.54-7.45 (m, 14H), 7.30-7.27 (dd, 2H) | 546.25 | 546.17 |
| 15 | δ = 7.90-7.88 (m, 2H), 7.78-7.74 (m, 4H), 7.54-7.45 (m, 16H), 7.32-7.27 (m, 1H), 7.18-7.15 (m, 4H) | 621.30 | 621.22 |
| 18 | δ = 8.20-8.17 (m, 2H), 8.04-7.98 (m, 4H), 7.93-7.89 (m, 2H), 7.78-7.75 (m, 4H), 7.56-7.45 (m, 16H), 7.41-7.39 (dd, 2H), 7.31-7.25 (m, 3H) | 775.33 | 775.27 |
| 24 | δ = 7.95-7.92 (m, 2H), 7.78-7.72 (m, 6H), 7.54-7.45 (m, 14H), 7.30-7.25 (m, 4H) | 646.26 | 646.22 |
| 27 | δ = 8.27-7.25 (m, 1H), 8.16-8.14 (m, 1H), 8.07-8.05 (m, 1H), 7.99-7.76 (m, 2H), 7.76-7.44 (m, 24H), 7.19-7.16 (m, 2H) | 721.28 | 721.25 |
| 28 | δ = 7.80-7.78 (m, 2H), 7.76-7.73 (m, 6H), 7.54 (d, 4H), 7.51-7.44 (m, 12H), 7.37-7.34 (m, 4H) | 608.26 | 608.23 |
| 31 | δ = 7.78-7.74 (m, 4H), 7.54 (d, 4H), 7.51-7.44 (m, 12H), 7.37-7.34 (m, 4H) | 612.29 | 612.25 |
| 34 | δ = 7.78-7.76 (m, 4H), 7.68-7.66 (dd, 2H), 7.58 (d, 1H), 7.65 (d, 1H), 7.54 (d, 4H), 7.51-7.37 (m, 16H), 7.33-7.30 (m, 2H), 7.28-7.22 (m, 4H), 7.15-7.07 (m, 6H) | 848.36 | 848.32 |
| 37 | δ = 8.30-8.28 (m, 2H), 8.08-8.06 (dd, 2H), 7.78-7.72 (m, 6H), 7.66-7.64 (m, 2H), 7.54-7.42 (m, 12H), 7.38-7.35 (m, 4H), 7.26-7.22 (m, 2H) | 714.25 | 714.21 |
| 39 | δ = 8.02-8.00 (m, 2H), 7.96-7.86 (m, 6H), 7.78-7.74 (m, 4H), 7.69-7.67 (m, 2H), 7.63-7.54 (m, 14H) | 632.26 | 632.23 |
| 41 | δ = 7.94-7.92 (m, 2H), 7.79-7.71 (m, 10H), 7.54-7.39 (m, 14H), 7.30-7.27 (m, 2H), | 712.26 | 712.22 |
| 44 | δ = 8.30 (s, 1H), 8.12 (s, 1H), 7.84-7.73 (m, 8H), 7.63-7.56 (m, 4H), 7.51-7.38 (m, 8H) | 534.22 | 534.18 |
| 46 | δ = 7.93-7.89 (dd, 2H), 7.83-7.80 (m, 2H), 7.77-7.72 (m, 4H), 7.66-7.63 (dd, 2H), 7.60-7.37 (m, 14H), 7.33-7.29 (m, 2H), 7.17-7.15 (dd, 2H) | 632.26 | 632.23 |
| 47 | δ = 7.78-7.73 (m, 4H), 7.61-7.58 (m, 2H), 7.54-7.41 (m, 16H), 7.31-7.27 (dd, 2H), 7.18-7.15 (dd, 2H), 1.64 (s, 6H) | 648.29 | 648.26 |
| 51 | δ = 7.96-7.93 (m, 2H), 7.78-7.72 (m, 5H), 7.65-7.63 (dd, 1H), 7.61-7.59 (m, 1H), 7.51-7.44 (m, 14H), 7.33-7.30 (m, 2H), 7.23-7.21 (dd, 1H), 0.44 (s, 6H) | 664.27 | 664.23 |
| 52 | δ = 8.03-8.01 (m, 1H), 7.96-7.94 (m, 1H), 7.84-7.82 (m, 1H), 7.76-7.66 (m, 8H), 7.69-7.66 (m, 2H), 7.60-7.44 (m, 13H), 7.35-7.33 (m, 1H), 7.13-7.10 (dd, 1H), 1.64 (s, 6H) | 698.33 | 698.27 |
| 56 | δ = 8.25 (s, 1H), 8.08-8.02 (m, 2H), 7.77-7.73 (m, 6H), 7.64-7.45 (m, 13H), 7.31-7.25 (m, 2H), 7.13-7.10 (dd, 1H), 1.65 (s, 6H) | 649.29 | 649.25 |
| 57 | δ = 7.94-7.91 (m, 1H), 7.80-7.71 (m, 6H), 7.64-7.38 (m, 18H), 7.33-7.30 (m, 1H), 7.22-7.19 (m, 1H), 7.13-7.10 (dd, 1H), 1.63 (s, 6H) | 698.31 | 698.27 |
| 58 | δ = 7.91-7.88 (m, 1H), 7.82-7.76 (m, 4H), 7.66-7.40 (m, 15H), 7.32-7.30 (m, 1H), 7.13-7.10 (dd, 1H), 6.91 (d, 1H), 6.72 (d, 1H), 1.66 (s, 6H) | 638.29 | 638.24 |
| 59 | δ = 7.95-7.93 (m, 1H), 7.79-7.72 (m, 4H), 7.65-7.45 (m, 14H), 7.31-7.28 (m, 2H), 7.21 (d, 1H), 7.13-7.10 (dd, 1H), 7.02 (d, 1H), 1.62 (s, 6H) | 654.26 | 654.21 |
| 63 | δ = 8.08-8.05 (m, 2H), 7.96-7.90 (m, 4H), 7.78-7.74 (m, 4H), 7.69-7.60 (m, 3H), 7.53-7.44 (m, 17H), 7.33-7.31 (m, 1H), 7.24-7.22 (m, 1H), 7.18-7.16 (dd, 1H), | 747.31 | 747.27 |

Example 1

As an anode, a substrate, on which 70/1,000/70 Å of ITO/Ag/ITO was deposited, was cut into a size of 50 mm×50 mm×0.5 mm and then ultrasonically washed the substrate using isopropyl alcohol and distilled water for 5 minutes, followed by irradiation of UV and exposure to ozone for cleaning for about 30 minutes. The glass substrate was then loaded onto a vacuum deposition device.

2-TNATA was vacuum deposited on the substrate as a hole-injecting material at a thickness of 600 Å, and 4,4'-bis [N-(1-naphthyl)-N-phenyl amino]biphenyl (NPB), which is a hole-transporting compound, was vacuum deposited thereon as a hole-transporting compound to form an HTL having a thickness of 1,000 Å.

Compound 1 was used as a green phosphorescent host, and Ir(ppy)$_3$ was used as a dopant, and they were simultaneously vacuum deposited on the HTL in a weight ratio of 91:9 to form an EML having a thickness of 250 Å. Then, BCP was vacuum deposited on the EML as a hole blocking compound at a thickness of 50 Å to form an HBL. Then, Alq$_3$ was vacuum deposited on the HBL at a thickness of 350 Å to form an ETL, and LiF, which is a halogenated alkali metal, was vacuum deposited at a thickness of 10 Å to form an EIL, and then Mg and Ag were vacuum deposited in a weight ratio of 90:10 and at a thickness of 120 Å to form an electrode to manufacture an organic light-emitting diode.

The OLED exhibited a driving voltage of 5.3 V, light-emission brightness of 5,210 cd/m², light-emission efficiency of 52.1 cd/A, and half-life of 60 hours at a current density of 10 mA/cm².

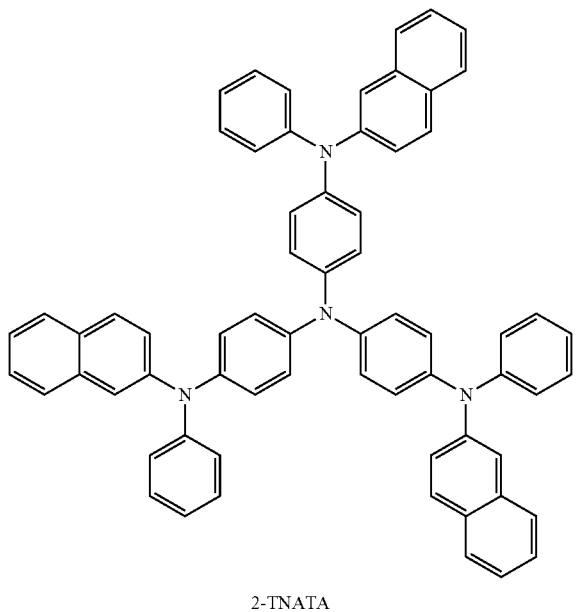

2-TNATA

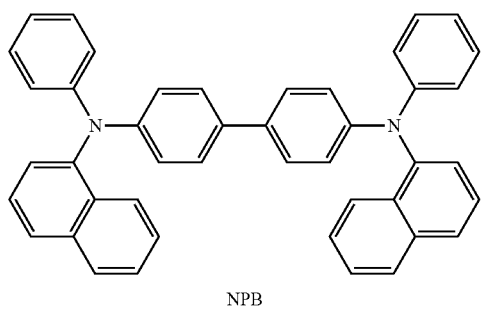

NPB

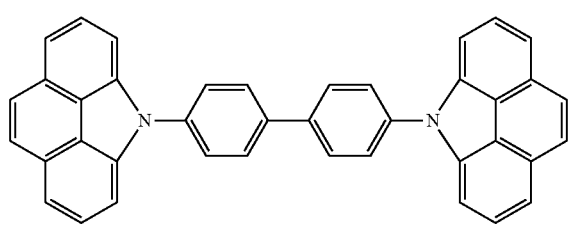

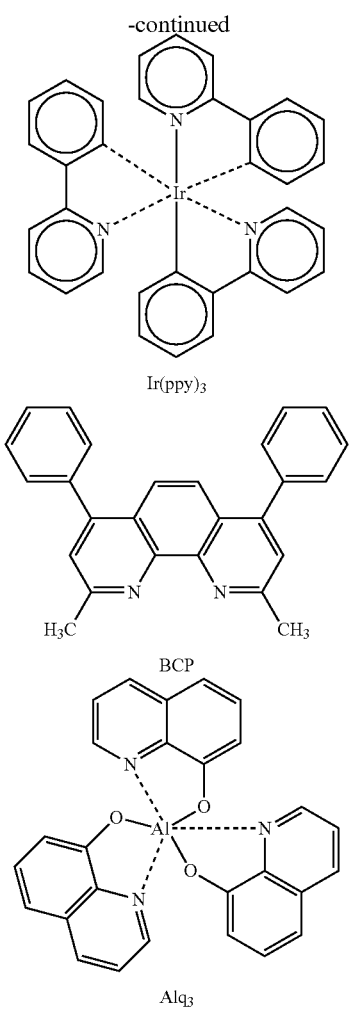

Ir(ppy)₃

BCP

Alq₃

Example 2

An OLED was manufactured in the same manner as in Example 1, except that Compound 8 was used instead of Compound 1 when forming an EML.

The OLED exhibited a driving voltage of 5.5 V, light-emission brightness of 5,392 cd/m², light-emission efficiency of 53.9 cd/A, and half-life of 69 hours at a current density of 10 mA/cm².

Example 3

An OLED was manufactured in the same manner as in Example 1 except that Compound 28 was used instead of Compound 1 when forming an EML.

The OLED exhibited a driving voltage of 5.5 V, light-emission brightness of 5,011 cd/m², light-emission efficiency of 50.1 cd/A, and half-life of 51 hours at a current density of 10 mA/cm².

Example 4

An OLED was manufactured in the same manner as in Example 1, except that Compound 39 was used instead of Compound 1 when forming an EML.

The OLED exhibited a driving voltage of 5.2 V, light-emission brightness of 5,561 cd/m$^2$, light-emission efficiency of 55.6 cd/A, and half-life of 55 hours at a current density of 10 mA/cm$^2$.

Example 5

When forming an HTL in Example 1, 4,4'-bis[N-(1-naphthyl)-N-phenylamino]biphenyl (hereinafter, NPB), which is a hole-transporting material, was vacuum deposited at a thickness of 1,350 Å. An OLED was manufactured in the same manner as in Example 1, except that Compound 18 was used as a red phosphorescent host, and bis(2-(2'-benzo[4,5-a]thienyl)pyridinato-N, C3') iridium acetylacetonate (BtpIr) were co-deposited in a weight ratio of 94:6 to form an EML having a thickness of 400 Å.

BtpIr

The OLED exhibited a driving voltage of 5.5 V, light-emission brightness of 2,420 cd/m$^2$, light-emission efficiency of 24.2 cd/A, and half-life of 103 hours at a current density of 10 mA/cm$^2$.

Example 6

An OLED was manufactured in the same manner as in Example 1, except that Compound 46 was used instead of Compound 18, when forming an EML.

The OLED exhibited a driving voltage of 5.4 V, light-emission brightness of 2,560 cd/m$^2$, light-emission efficiency of 25.0 cd/A, and half-life of 100 hours at a current density of 10 mA/cm$^2$.

Example 7

An OLED was manufactured in the same manner as in Example 1, except that Compound 56 was used instead of Compound 18, when forming an EML.

The OLED exhibited a driving voltage of 5.5 V, light-emission brightness of 2,390 cd/m$^2$, light-emission efficiency of 23.9 cd/A, and half-life of 109 hours at a current density of 10 mA/cm$^2$.

Example 8

An OLED was manufactured in the same manner as in Example 1, except that Compound 63 was used instead of Compound 18, when forming an EML.

The OLED exhibited a driving voltage of 5.3 V, light-emission brightness of 2,350 cd/m$^2$, light-emission efficiency of 23.5 cd/A, and half-life of 115 hours at a current density of 10 mA/cm$^2$.

Comparative Example 1

An OLED was manufactured in the same manner as in Example 1, except that 4,4'-N,N'-dicarbazolbiphenyl (CBP), which is a green phosphorescent host, was used instead of Compound 1, when forming an EML.

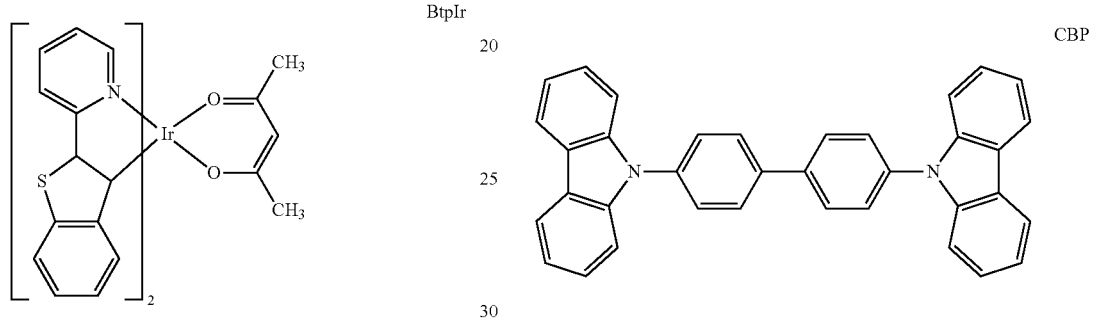

CBP

The OLED exhibited a driving voltage of 6.5 V, light-emission brightness of 3,210 cd/m$^2$, light-emission efficiency of 32.1 cd/A, and half-life of 32 hours at a current density of 10 mA/cm$^2$.

Comparative Example 2

An OLED was manufactured in the same manner as in Example 5, except that 4,4'-N,N'-dicarbazolbiphenyl (CBP), which is a red phosphorescent host, was used instead of Compound 18, when forming an EML.

The OLED exhibited a driving voltage of 6.8 V, light-emission brightness of 1,643 cd/m$^2$, light-emission efficiency of 16.4 cd/A, and half-life of 45 hours at a current density of 10 mA/cm$^2$.

As a result of using compounds having the structure of Formula 1 as green and red phosphorescent materials of the EML, the OLEDs exhibited substantial improvements in driving voltage and excellent I-V-L characteristics with improved efficiency compared to CBP, which is another material. For example, improvements were excellent for lifespan of the OLEDs, thereby substantially improving the lifespan of the OLEDs. Representative characteristics and lifespan of the OLEDs are summarized in Table 2 below.

TABLE 2

|  | Host or electron-transporting material | Driving voltage (V) | Current density (mA/cm$^2$) | Brightness (cd/m$^2$) | Efficiency (cd/A) | Emitted light color | Lifespan LT97 (hr) |
| --- | --- | --- | --- | --- | --- | --- | --- |
| Example 1 | Compound 1 | 5.3 | 10 | 5,210 | 52.1 | green | 60 hr |
| Example 2 | Compound 8 | 5.5 | 10 | 5,392 | 53.9 | green | 69 hr |
| Example 3 | Compound 28 | 5.5 | 10 | 5,011 | 50.1 | green | 51 hr |
| Example 4 | Compound 39 | 5.2 | 10 | 5,561 | 55.6 | green | 55 hr |
| Example 5 | Compound 18 | 5.5 | 10 | 2,420 | 24.2 | red | 103 hr |
| Example 6 | Compound 46 | 5.4 | 10 | 2,560 | 25.0 | red | 100 hr |
| Example 7 | Compound 56 | 5.5 | 10 | 2,390 | 23.9 | red | 109 hr |

TABLE 2-continued

| | Host or electron-transporting material | Driving voltage (V) | Current density (mA/cm$^2$) | Brightness (cd/m$^2$) | Efficiency (cd/A) | Emitted light color | Lifespan LT97 (hr) |
|---|---|---|---|---|---|---|---|
| Example 8 | Compound 63 | 5.3 | 10 | 2,350 | 23.5 | red | 115 hr |
| Comparative Example 1 | CBP | 6.5 | 10 | 3,210 | 32.1 | green | 32 hr |
| Comparative Example 2 | CBP | 6.8 | 10 | 1,643 | 16.4 | red | 45 hr |

As described above, according to an embodiment, the heterocyclic compound represented by Formula 1 above may exhibit excellent light-emission capability and thus, the heterocyclic compound may be useful as an emission material that is suitable for fluorescent and phosphorescent devices of all colors such as red, green, blue, and white. By using the heterocyclic compound, an OLED having high efficiency, low voltage, high brightness, and a long lifespan may be manufactured.

The embodiments may provide a material that has excellent electrical stability, high charge-transporting ability or light-emitting ability, high glass transition temperature, and is capable of preventing crystallization.

The embodiments may provide a material that has excellent electrical properties, high charge-transporting ability, light-emitting ability, and high glass transition temperature. The material may be useful for an electron-transporting material or an electron-injecting material that is suitable for fluorescent and phosphorescent devices of all colors such as red, green, blue, and white.

The embodiments may provide an organic light-emitting device having high efficiency, low driving voltage, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1 below:

<Formula 1>

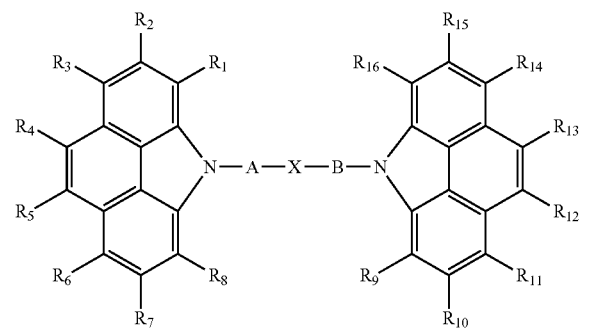

In Formula 1, $R_1$ to $R_{16}$ are each independently a hydrogen or a deuterium, X, A, and B are each independently a single bond, a substituted or unsubstituted $C_6$-$C_{60}$ arylene group, a substituted or unsubstituted $C_2$-$C_{60}$ heteroarylene group, and a substituted or unsubstituted $C_6$-$C_{60}$ condensed polycyclic divalent connector, provided that X, A, and B are not all simultaneously single bonds.

2. The heterocyclic compound as claimed in claim 1, wherein, in Formula 1 above, X, A, and B are each independently one of a single bond or a group represented by Formulae 2a to 2f below:

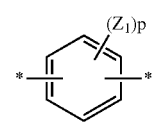

2a

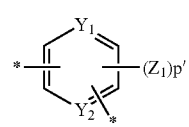

2b

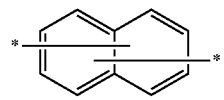

2c

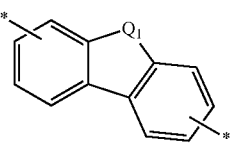

2d

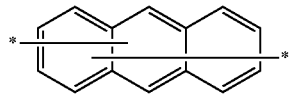

2e

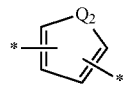

2f wherein, in Formulae 2a to 2f, $Q_1$ is —$CR_{31}R_{32}$—, —$SiR_{41}R_{42}$—, —O—, —S—, or —$NR_{51}$;

$Q_2$ is O or S;

$Y_1$ and $Y_2$ are each independently CH or N;

$R_{31}$, $R_{32}$, $R_{41}$, $R_{42}$, $R_{51}$, and $Z_1$ are each independently a hydrogen, a deuterium, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen group, a cyano group, a nitro group, a hydroxy group, or a carboxy group, and, in a case of a plurality of $Z_1$s, each of the $Z_1$s are the same or are different from each other;

p is an integer of 1 to 4;

p' is 1 or 2; and

\* represents a binding site.

3. The heterocyclic compound as claimed in claim 2, wherein $R_{31}$, $R_{32}$, $R_{41}$, $R_{42}$, $R_{51}$ and $Z_1$ of Formulae 2a to 2f are each independently a hydrogen, a deuterium, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, or a halogen group.

4. The heterocyclic compound as claimed in claim 2, wherein:

at least one of X, A, or B is a group represented by Formula 2d, and $Q_1$ of Formula 2d is —$CR_{31}R_{32}$— or —$NR_{51}$—.

5. The heterocyclic compound as claimed in claim 1, wherein $R_1$ to $R_{16}$ in Formula 1 are hydrogen.

6. The heterocyclic compound as claimed in claim 1, wherein the compound represented by Formula 1 is one of compounds 1, 8, 18, 28, 39, 46, 56, or 63, below:

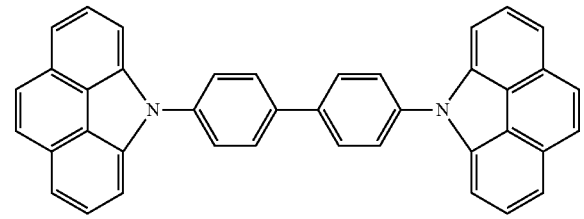

1

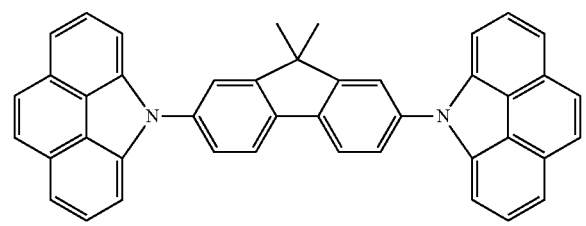

8

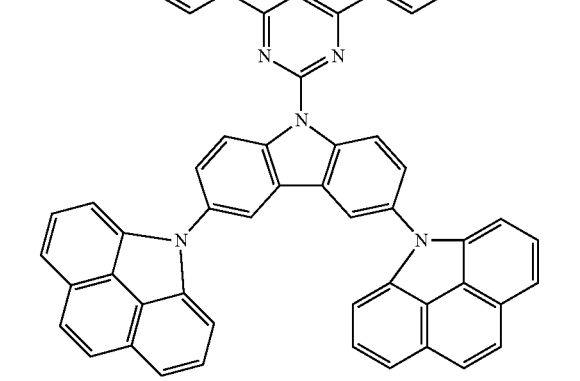

18

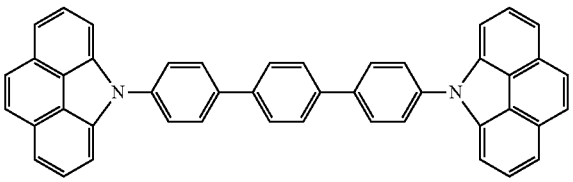

28

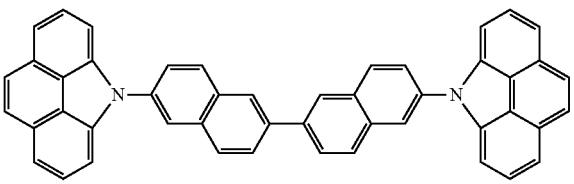

39

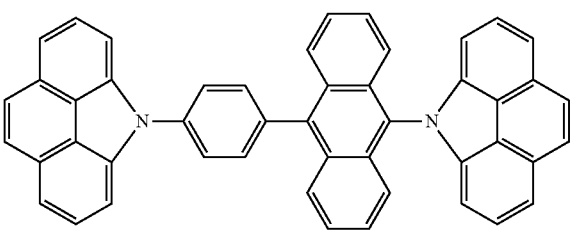

46

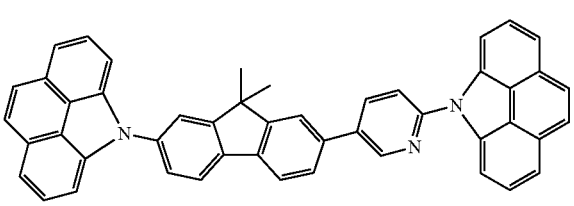

56

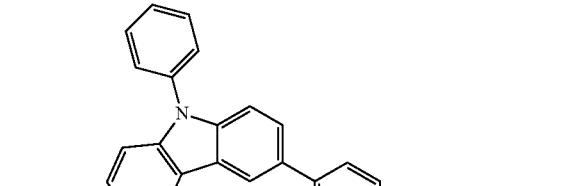

63

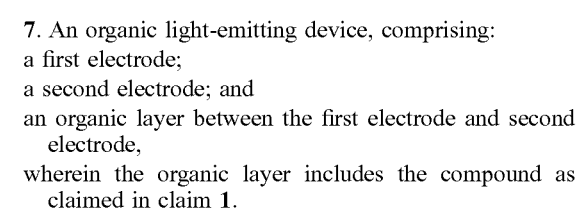

7. An organic light-emitting device, comprising:
   a first electrode;
   a second electrode; and
   an organic layer between the first electrode and second electrode,
   wherein the organic layer includes the compound as claimed in claim 1.

8. The organic light-emitting device as claimed in claim 7, wherein the organic layer includes an emission layer.

9. The organic light-emitting device as claimed in claim 7, wherein the organic layer includes a green emission layer or a red emission layer.

10. The organic light-emitting device as claimed in claim 7, wherein:
the organic layer includes an emission layer, and further includes one of an electron-injecting layer, an electron-transporting layer, and a functional layer having both electron injection and electron transporting capabilities, a hole-injecting layer, a hole-transporting layer, or a functional layer having both hole-injecting and hole-transporting capabilities, and
the emission layer includes an anthracene-based compound, an arylamine-based compound, or a styryl-based compound.

11. The organic light-emitting diode as claimed in claim 7, wherein:
the organic layer includes an emission layer, and further includes one of an electron-injecting layer, an electron-transporting layer, a functional layer having both electron injecting and electron transporting capabilities, a hole-injecting layer, a hole-transporting layer, or a functional layer having both hole injecting and hole transporting capabilities, and
any one layer of a red layer, a green layer, a blue layer, or a white layer of the emission layer includes a phosphorescent compound.

12. The organic light-emitting diode as claimed in claim 11, wherein:
the organic layer includes one of the hole-injecting layer, the hole-transporting layer, or the functional layer having both hole injecting and hole transporting capabilities, and
the hole-injecting layer, the hole-transporting layer, or the functional layer having both hole injecting and hole transporting capabilities includes a charge-generating material.

13. The organic light-emitting diode as claimed in claim 12, wherein the charge-generating material is a p-dopant.

14. The organic light-emitting diode as claimed in claim 13, wherein the p-dopant includes a quinone derivative.

15. The organic light-emitting diode as claimed in claim 13, wherein the p-dopant includes a metal oxide.

16. The organic light-emitting diode as claimed in claim 13, wherein the p-dopant includes a cyano group containing compound.

17. The organic light-emitting diode as claimed in claim 7 wherein the organic layer includes an electron-transporting layer, the electron-transporting layer including an electron-transporting material and a metal complex.

18. The organic light-emitting diode as claimed in claim 17, wherein the metal complex includes lithium quinolate or Compound 203 below:

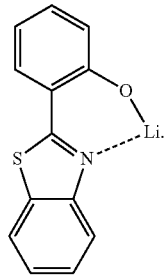

<Compound 203>

19. The organic light-emitting diode as claimed in claim 7 wherein the organic layer including the heterocyclic compound is formed using a wet process.

20. A flat display device comprising the organic light-emitting diode as claimed in claim 7, wherein the first electrode of the organic light-emitting diode is electrically connected to a source electrode or a drain electrode of a thin film transistor.

* * * * *